United States Patent
Delaney et al.

(10) Patent No.: US 9,350,921 B2
(45) Date of Patent: May 24, 2016

(54) STRUCTURED ILLUMINATION PROJECTION WITH ENHANCED EXPOSURE CONTROL

(71) Applicant: Mitutoyo Corporation, Kawasaki-shi, Kanagawa-ken (JP)

(72) Inventors: Mark Lawrence Delaney, Shoreline, WA (US); Paul Gerard Gladnick, Seattle, WA (US)

(73) Assignee: Mitutoyo Corporation, Kawasaki-shi (JP)

( * ) Notice: Subject to any disclaimer, the term of this patent is extended or adjusted under 35 U.S.C. 154(b) by 455 days.

(21) Appl. No.: 13/912,116

(22) Filed: Jun. 6, 2013

(65) Prior Publication Data

US 2014/0362203 A1 Dec. 11, 2014

(51) Int. Cl.
*H04N 5/235* (2006.01)
*H04N 5/225* (2006.01)
(Continued)

(52) U.S. Cl.
CPC ............. *H04N 5/2354* (2013.01); *G01N 21/00* (2013.01); *H04N 5/2256* (2013.01)

(58) Field of Classification Search
CPC . H04N 13/0203; H04N 5/265; H04N 5/2354; H04N 5/235; H04N 5/225; H04N 5/2256; H04N 5/228; G02B 21/06; G06K 9/40; G01J 1/58; G01N 21/00
See application file for complete search history.

(56) References Cited

U.S. PATENT DOCUMENTS

| 6,376,818 | B1 | 4/2002 | Wilson |
| 6,819,415 | B2 | 11/2004 | Gerstner |
| 7,115,848 | B1 | 10/2006 | Zinter |

(Continued)

FOREIGN PATENT DOCUMENTS

| DE | 10 2005 052 061 A1 | 5/2007 |
| EP | 1 739 471 B1 | 9/2007 |

(Continued)

OTHER PUBLICATIONS

"3D Metrology," Brochure, Forth Dimension Displays, <http://www.forthdd.com/system/files/SXGA-3DM-UK%20Rolling%20format.pdf>, [believed to be available as early as Mar. 26, 2012], 4 pages.

(Continued)

*Primary Examiner* — Dramos I Kalapodas
(74) *Attorney, Agent, or Firm* — Christensen O'Connor Johnson Kindness PLLC

(57) ABSTRACT

A method for controlling a structured illumination pattern generating portion is provided for illuminating a workpiece during an image acquisition by a camera in a precision machine vision inspection system. A controllable spatial light modulator (e.g., a digital light processing projector) is part of the generating portion for generating the structured illumination pattern. The pattern may comprise an array of stripes including a sinusoidal gray level intensity variation across each stripe. An overall image exposure is increased by repeating a complete structured illumination pattern generation iteration, including gray level variation, a plurality of times during an image integration period. Structured illumination microscopy techniques for determining a workpiece surface profile may benefit, wherein multiple (e.g., 3 or 4) images are acquired at respective focus positions to be analyzed, by using the method to project a different phase of a structured light pattern for each of the multiple images.

20 Claims, 9 Drawing Sheets

(51) Int. Cl.
G01N 21/00 (2006.01)
H04N 5/265 (2006.01)

(56) References Cited

U.S. PATENT DOCUMENTS

| | | | |
|---|---|---|---|
| 7,120,286 B2 | 10/2006 | Yu | |
| 7,335,866 B2 | 2/2008 | Backs | |
| 7,400,414 B2 | 7/2008 | Tobiason | |
| 7,570,795 B2 | 8/2009 | Yu | |
| 7,668,388 B2 | 2/2010 | Bryll | |
| 7,723,657 B2 | 5/2010 | Altendorf | |
| 7,728,961 B2 | 6/2010 | Watson | |
| 8,041,142 B2 | 10/2011 | Schäfer | |
| 8,045,002 B2 | 10/2011 | Gladnick | |
| 8,111,905 B2 | 2/2012 | Campbell | |
| 8,111,938 B2 | 2/2012 | Bryll | |
| 8,317,347 B2 | 11/2012 | Gladnick | |
| 8,509,879 B2 * | 8/2013 | Durkin | A61B 5/0073 600/407 |
| 2003/0122955 A1 * | 7/2003 | Neidrich | G02B 23/02 348/340 |
| 2003/0223083 A1 * | 12/2003 | Geng | G01B 11/2509 356/603 |
| 2005/0244078 A1 * | 11/2005 | Magarill | G02B 27/60 382/274 |
| 2007/0269134 A1 | 11/2007 | Ruanaidh | |
| 2008/0037032 A1 * | 2/2008 | Scogin | G01B 11/25 356/603 |
| 2008/0218817 A1 * | 9/2008 | Grygier | G03H 1/028 359/9 |
| 2009/0147354 A1 * | 6/2009 | Arbuckle | G02B 21/16 359/368 |
| 2011/0133054 A1 | 6/2011 | Campbell | |
| 2011/0182529 A1 * | 7/2011 | Kempe | G01N 21/6458 382/274 |
| 2012/0154571 A1 | 6/2012 | Bryll | |
| 2012/0176478 A1 * | 7/2012 | Wang | G01B 11/2536 348/47 |
| 2013/0162806 A1 | 6/2013 | Ding | |
| 2013/0162807 A1 | 6/2013 | Bryll | |
| 2013/0342886 A1 * | 12/2013 | Cooper | G02B 21/082 359/204.3 |
| 2014/0132721 A1 * | 5/2014 | Martinez Bauza | G01B 11/25 348/46 |
| 2014/0313576 A1 * | 10/2014 | Uhl | G02B 21/14 359/385 |

FOREIGN PATENT DOCUMENTS

| | | |
|---|---|---|
| EP | 1 556 728 B1 | 7/2008 |
| WO | 92/14118 A1 | 8/1992 |
| WO | 98/45745 A1 | 10/1998 |

OTHER PUBLICATIONS

"3D Metrology," Forth Dimension Displays, <http://www.forthdd.com/applications/3d-metrology>, [retrieved Apr. 13, 2013], 1 page.

"ApoTome: Suddenly Everything Looks Different," Carl Zeiss Light Microscopy, Gottingen, Germany, Document No. 60-2-0025 e, 20 pages, as early as Feb. 2009.

Caldwell, M., "Object Resolution Enhancement From Structured Illumination Microscopy," UCL CoMPLEX (University College London, Centre for Mathematics and Physics in the Life Sciences and Experimental Biology) <http://www.ucl.ac.uk/~ucbpmbc/downloads/>, Nov. 2007, 24 pages.

Cartwright, N., et al., "The Use of LCoS Microdisplays in 3D Optical Surface Metrology Systems," <http://www.forthdd.com/system/files/Use%20of%20LCoS%20in%20Metrology%20Systems.pdf>, [believed to be available as early as Oct. 3, 2011], 7 pages.

"CBT-90 LEDs," CBT-90 Binning and Labeling Datasheet, No. PDS-001694 Rev 06, © 2013 Luminus Devices, Inc., Billerica, Mass., <http://www.luminus.com/products /Luminus_CBT90_BinningLabeling.pdf>, 9 pages.

"CBT-90 LEDs," CBT-90 Product Datasheet, No. PDS-001230 Rev 10, © 2013 Luminus Devices, Inc., Billerica, Mass.,<http://www.luminus.com/products/Luminus_CBT90C_Datasheet.pdf>, 17 pages.

"DLP® 0.55 XGA Series 450 DMD," Datasheet, Product Folder Links: DLP5500, Texas Instruments, Dallas, Tex., <http://www.ti.com/lit/ds/symlink/dlp500.pdf>, DLPS013D—Apr. 2010—Revised Oct. 2012, with Package Option Addendum of Mar. 2013, 27 pages.

"DLP5500, DLPC200, DLPA200: DLP® 0.55 XGA Chipset," Data Manual DLPZ004B, Texas Instruments, Dallas, Tex., <http://www.ti.com/lit/er/dlpz004b/dlpz004b.pdf>, Jun. 2010—Revised Feb. 2012, 56 pages.

"Generating Greyscale," Forth Dimension Displays, <http://www.forthdd.com/technology/generating-greyscale>, [retrieved Apr. 13, 2013], 2 pages.

McCallum, M., "The Use of LCoS Microdisplays in 3D Optical Surface Metrology Systems," Forth Dimension Displays Presentation at the SID-ME Chapter Spring Meeting on Microdisplays, Applications, and Optics, Jena, Germany, Mar. 13-14, 2008, 12 pages.

"Microdisplay Operation," Forth Dimension Displays, <http://www.forthdd.com/technology/microdisplay-operation>, [retrieved Apr. 13, 2013], 1 page.

"Optical Principle," Forth Dimension Displays, <http://www.forthdd.com/technology/optical-principle>, [retrieved Apr. 13, 2013], 1 page.

"OptiGrid®: Structured-Illumination Microscopy," Brochure 37-00-00-450, Qioptiq Imaging Solutions, Sep. 2006, <http://www.aic-imagecentral.com/products/pdfs/OptiGrid_Brochure.pdf>, [retrieved Feb. 2009], 8 pages.

"Sensofar®: PLu neox—3D Optical Profiler," Sensofar-Tech, S.L., Terrassa, Spain, <http://www.sensofar.com/sensofar/pdf/Plu_neox.pdf>, [retrieved Aug. 8, 2013], 1 page.

"Technology," Forth Dimension Displays, <http://www.forthdd.com/technology>, [retrieved Apr. 13, 2013], 1 page.

Vogel, M., et al., "Structured-Illumination Microscopy on Technical Surfaces: 3D Metrology With Nanometer Sensitivity," Proceedings of SPIE, Optical Measurement Systems for Industrial Inspection VII, Munich, May 23, 2011, vol. 8082, pp. 80820S-1-80820S-6.

Wilson, T., et al., "Real-Time Three-Dimensional Imaging of Macroscopic Structures," Journal of Microscopy 191(Pt. 2):116-118, Aug. 1998.

* cited by examiner

STRUCTURED ILLUMINATION PROJECTION WITH ENHANCED EXPOSURE CONTROL

BACKGROUND

Precision machine vision inspection systems (or "vision systems" for short) can be utilized to obtain precise dimensional measurements of inspected objects and to inspect various other object characteristics. Such systems may include a computer, a camera and optical system, and a precision stage that is movable in multiple directions to allow workpiece inspection. One exemplary prior art system that can be characterized as a general-purpose "off-line" precision vision system is the commercially available QUICK VISION® series of PC-based vision systems and QVPAK® software available from Mitutoyo America Corporation (MAC), located in Aurora, Ill. The features and operation of the QUICK VISION® series of vision systems and the QVPAK® software are generally described, for example, in the QVPAK 3D CNC Vision Measuring Machine User's Guide, published January 2003, and the QVPAK 3D CNC Vision Measuring Machine Operation Guide, published September 1996, each of which is hereby incorporated by reference in their entirety. This type of system is able to use a microscope-type optical system and move the stage so as to provide inspection images of either small or relatively large workpieces at various magnifications.

General purpose precision machine vision inspection systems, such as the QUICK VISION™ system, are also generally programmable to provide automated video inspection. U.S. Pat. No. 6,542,180 (the '180 patent) teaches various aspects of such automated video inspection and is incorporated herein by reference in its entirety. As taught in the '180 patent, automated video inspection metrology instruments generally have a programming capability that allows an automatic inspection event sequence to be defined by the user for each particular workpiece configuration. This can be implemented by text-based programming, for example, or through a recording mode which progressively "learns" the inspection event sequence by storing a sequence of machine control instructions corresponding to a sequence of inspection operations performed by a user with the aid of a graphical user interface, or through a combination of both methods. Such a recording mode is often referred to as "learn mode," "training mode," or "record mode." Once the inspection event sequence is defined in "learn mode," such a sequence can then be used to automatically acquire (and additionally analyze or inspect) images of a workpiece during "run mode."

The machine control instructions including the specific inspection event sequence (i.e., how to acquire each image and how to analyze/inspect each acquired image) are generally stored as a "part program" or "workpiece program" that is specific to the particular workpiece configuration. For example, a part program defines how to acquire each image, such as how to position the camera relative to the workpiece, at what lighting level, at what magnification level, etc. Further, the part program defines how to analyze/inspect an acquired image, for example, by using one or more video tools such as edge/boundary detection video tools.

Video tools (or "tools" for short) and other graphical user interface features may be used manually to accomplish manual inspection and/or machine control operations (in "manual mode"). Their set-up parameters and operation can also be recorded during learn mode in order to create automatic inspection programs or "part programs." Video tools may include, for example, edge/boundary detection tools, autofocus tools, shape or pattern matching tools, dimension measuring tools, and the like. It is generally desirable that complex hardware and software operations and/or analysis are performed automatically (e.g., without requiring user observation and/or intervention) in association with various video tools and/or selectable operating modes. In that case, relatively unskilled users may easily and "transparently" implement such complex operations and/or analysis to achieve better measurement accuracy and/or reliability.

Accuracies in the micron or sub-micron range are often desired in such systems. This is particularly challenging with regard to Z-height measurements. Z-height measurements (along the optical axis of the camera system) are generally derived from a "best focus" position, such as that determined by an autofocus tool. Determining a best focus position is a relatively complex process that generally depends on combining and/or comparing information derived from multiple images. Thus, the level of precision and reliability achieved for Z-height measurements is often less than that achieved for the X and Y measurement axes, where measurements are typically based on feature relationships within a single image. Recently, known techniques generally referred to as "structured illumination microscopy" (SIM) methods are being incorporated in microscopic measurement and inspection systems, in order to increase their measurement resolution and/or accuracy beyond the optical limits normally associated with simple imaging (e.g., to the micron and submicron level.)

Briefly, many SIM methods include projecting a pattern of light stripes onto a workpiece in a first image, and then shifting that pattern on the workpiece transversely to the stripes in a second image, and so on for a third image, or more. The resulting images may be analyzed according to known methods to improve the surface measurement resolution, as described in greater detail below. Such techniques may enhance X, Y, and/or Z measurements. However, the systems and methods used in known structured illumination pattern (SIP) generating subsystems (e.g., for forming and shifting the patterns) have so far limited the economy, versatility, and/or resolution and accuracy improvements of practical SIM systems in undesirable ways. In some methods of analysis, it is desirable for the stripes to exhibit a sinusoidal intensity profile across the stripes. The article "Autoexposure for Three-Dimensional Shape Measurement Using a Digital-Light-Processing Projector," by Ekstrand and Zhang in Optical Engineering 50(12), 123603 (December 2011), which is hereby incorporated herein in its entirety as a reference indicative of the state of the art, states:

> Development of a method that can automatically adjust image exposure is vital for high-precision three-D shape measurement. Adjusting the projected fringe pattern intensity is one of the options . . . . However, the fringe pattern is typically restricted to eight bits (256 grayscale values). Moreover, changing the maximum grayscale value usually affects the signal to noise ratio (SNR) of the measurement because the fringe contrast changes . . . . Therefore, it seems that adjusting the camera exposure time is the best option. However, for conventional sinusoidal fringe patterns displayed on a digital-light-processing "DLP" projector, the camera exposure time cannot be arbitrarily chosen because the projector relies on time modulation for the generation of grayscale values between zero and 255 . . . . . The smallest step to adjust the camera exposure time is its channel projection time (e.g., 8.33 ms for a 120-Hz projector). This step size is typically 1 to 2 orders of magnitude larger than the step size needed for practical exposure adjustment.

Some have solved this problem by using a prefabricated grayscale projection mask that effectively includes more than 8 bit resolution. The image exposure can be controlled by the exposure time Ekstrand and Zhang propose a solution to this problem that includes a projector defocusing technique. Their technique may use non-sinusoidal structured patterns (e.g., including binary patterns). The sinusoidal stripe patterns are realized by properly defocusing the projector. Because this defocusing technique alleviates the grayscale generation demands on the DLP, an "arbitrary" exposure time can be used with the DLP in order to achieve a desired image exposure.

While the foregoing solutions allow projecting a sinusoidal stripe pattern with a versatile exposure time, they have undesirable characteristics. For example, a "fixed" mask lacks versatility and requires an expensive and bulky mechanical translation system in order to provide the desired shifts of the pattern position on the workpiece. The defocusing technique of Ekstrand and Zhang may require additional and/or adjustable optical elements to provide the defocus, and/or may limit versatility in terms of minimum "defocused" stripe spacing, and/or may cause undesirable and/or unpredictable interactions with the focus variations used for Z height "points from focus" techniques used in some precision machine vision inspection systems. Thus, an improved method for economically generating a structured illumination pattern (SIP) that includes good grayscale resolution at a wide variety of exposure levels would be desirable.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

Figure 1:
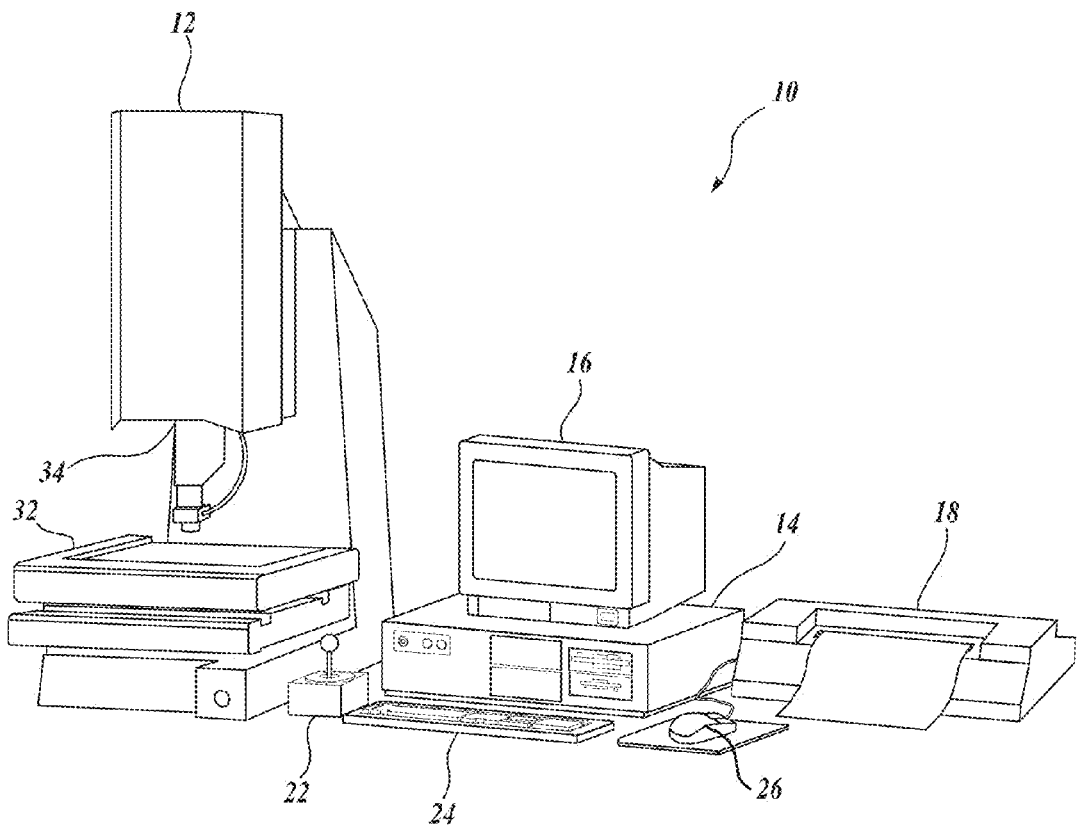
FIG. 1 is a diagram showing various typical components of a general purpose precision machine vision inspection system.

A method is provided for controlling a structured illumination pattern generating portion used to illuminate a workpiece with a structured illumination pattern during an image acquisition by a camera portion in a precision machine vision inspection system. The structured illumination pattern generating portion comprises a structured illumination pattern controller, a controllable spatial light modulator (SLM), and a light generator. The controllable SLM (e.g., a digital light processing array, such as a micro mirror array) is controlled for generating the structured illumination pattern, and the light generator emits radiation to the SLM. An image is acquired during an image integration period of the camera. The overall exposure is increased during the image integration period by a first exposure increment by generating a first complete structured illumination pattern iteration including gray level variations. The overall exposure is further increased during the image integration period by at least a second exposure increment by generating at least a second complete structured illumination pattern iteration including gray level variations.

In various implementations, the second exposure increment and the first exposure increment may be substantially the same. The light generator may be operated to emit substantially the same radiation intensity during the first and second complete structured illumination pattern iterations. A ratio of the radiation intensity to a maximum controllable radiation intensity may be greater than 0.6. The structured illumination patterns may comprise an array of stripes including an approximately sinusoidal variation in gray level intensity across a stripe.

The at least a second exposure increment may further comprise a least-significant bit (LSB) exposure increment that is less than the first and second exposure increments. The method may further comprise operating the light generator to emit a first radiation intensity during the first and second complete structured illumination pattern iteration, and to emit an LSB radiation intensity that is less than the first radiation intensity during the complete structured illumination pattern iteration corresponding to the LSB exposure increment.

The image integration period of the camera may be a time period TIP, and the method may further comprise generating each complete structured illumination pattern iteration including gray level variations within a respective time period TCPi, wherein each respective time period TCPi is at most Ti/4. At least one of the respective time periods TCPi may correspond to the shortest possible time period allowed by the structured illumination pattern generating portion.

The image integration period of the camera may be a time period TIP comprising N equal subperiods TCPn, and the method may further comprise generating each complete structured illumination pattern iteration including gray level variations within a respective subperiod TCPn. The structured illumination pattern (SIP) generating portion may further be operated such that no exposure increment occurs within at least one respective subperiod TCPn.

Generating the first complete structured illumination pattern iteration may comprise generating a first pattern subdivision exposure sequence comprising a plurality of respective pattern portions exposed using respective first iteration intensities of radiation from the light generator during respective first iteration subdivision times. Generating the at least a second complete structured illumination pattern iteration including gray level variations may comprise generating at least a second pattern subdivision exposure sequence comprising a plurality of respective pattern portions exposed using respective iteration intensities of radiation from the light generator during respective iteration subdivision times. At least the first and a second pattern subdivision exposure sequences may be identical.

The at least a second exposure increment may comprise an LSB exposure increment that is different than the first and second exposure increments. The method may further comprise generating the LSB exposure increment by generating a complete structured illumination pattern iteration including gray level variations by generating an LSB pattern subdivision exposure sequence comprising a plurality of respective pattern portions exposed using respective LSB iteration intensities of radiation from the light generator during respective LSB iteration subdivision times. The method may further include at least one of (a) making the respective LSB iteration intensities less than the corresponding respective first and second iteration intensities, and (b) making the respective LSB iteration subdivision times less than the corresponding first and second iteration subdivision times. Alternatively, the method may further include at least one of (a) making the respective LSB iteration intensities greater than the corresponding respective first and second iteration intensities, and (b) making the respective LSB iteration subdivision times greater than the corresponding first and second iteration subdivision times.

The image integration period of the camera may be a time period TIP comprising N equal subperiods TCPn, and the first and second complete structured illumination pattern iterations may correspond to approximately a 100% duty cycle and may be provided during one subperiod TCPn each. An LSB structured illumination pattern corresponding to a duty cycle between 0% and 100% may be provided during one subperiod TCPn, with structured illumination patterns corresponding to either a 0% or 100% duty cycle being provided during the remaining subperiods TCPn of the time period TIP.

The acquired image may be one of a stack of images that is acquired. The stack of images may be acquired utilizing structured illumination microscopy such that for each stack image acquired at a given Z height, the SIP that is provided by the SIP generating portion is phase shifted relative to the SIPs that are provided for the other stack images at the corresponding Z height. The first and second complete structured illumination pattern iterations may be repeated for the acquisition of each image in the stack.

Various embodiments of the invention are described below. The following description provides specific details for a thorough understanding and an enabling description of these embodiments. One skilled in the art will understand, however, that the invention may be practiced without many of these details. In addition, some well known structures or functions may not be shown or described in detail, so as to avoid unnecessarily obscuring the relevant description of the various embodiments. The terminology used in the description presented below is intended to be interpreted in its broadest reasonable manner, even though it is being used in conjunction with a detailed description of certain specific embodiments of the invention.

FIG. 1 is a block diagram showing various typical components of one exemplary precision machine vision inspection system 10 usable in accordance with methods described herein. The machine vision inspection system 10 includes a vision components portion 12 that is operably connected to exchange data and control signals with a controlling computer system 14. The controlling computer system 14 is further operably connected to exchange data and control signals with a monitor or display 16, a printer 18, a joystick 22, a keyboard 24, and a mouse 26. The monitor or display 16 may display a user interface suitable for controlling and/or programming the operations of the machine vision inspection system 10. It will be appreciated that in various embodiments, a touchscreen tablet or the like may be substituted for and/or redundantly provide the functions of any or all of the computer system 14, the display 16, the joystick 22, the keyboard 24, and the mouse 26.

Those skilled in the art will appreciate that the controlling computer system 14 may generally consist of any computing system or device. Suitable computing systems or devices may include personal computers, server computers, minicomputers, mainframe computers, distributed computing environments that include any of the foregoing, and the like. Such computing systems or devices may include one or more processors that execute software to perform the functions described herein. Processors include programmable general-purpose or special-purpose microprocessors, programmable controllers, application-specific integrated circuits (ASICs), programmable logic devices (PLDs), or the like, or a combination of such devices. Software may be stored in memory, such as random access memory (RAM), read-only memory (ROM), flash memory, or the like, or a combination of such components. Software may also be stored in one or more storage devices, such as magnetic or optical based disks, flash memory devices, or any other type of non-volatile storage medium for storing data. Software may include one or more program modules which include routines, programs, objects, components, data structures, and so on that perform particular tasks or implement particular abstract data types. In distributed computing environments, the functionality of the program modules may be combined or distributed across multiple computing systems or devices and accessed via service calls, either in a wired or wireless configuration.

The vision components portion 12 includes a moveable workpiece stage 32 and an optical imaging system 34 which may include a zoom lens or interchangeable lenses. The zoom lens or interchangeable lenses generally provide various magnifications for the images provided by the optical imaging system 34. The machine vision inspection system 10 is generally comparable to the QUICK VISION® series of vision systems and the QVPAK® software discussed above, and similar state-of-the-art commercially available precision machine vision inspection systems. The machine vision inspection system 10 is also described in commonly assigned U.S. Pat. Nos. 7,454,053, 7,324,682, 8,111,905, and 8,111,938, which are each incorporated herein by reference in their entireties.

Figure 2:
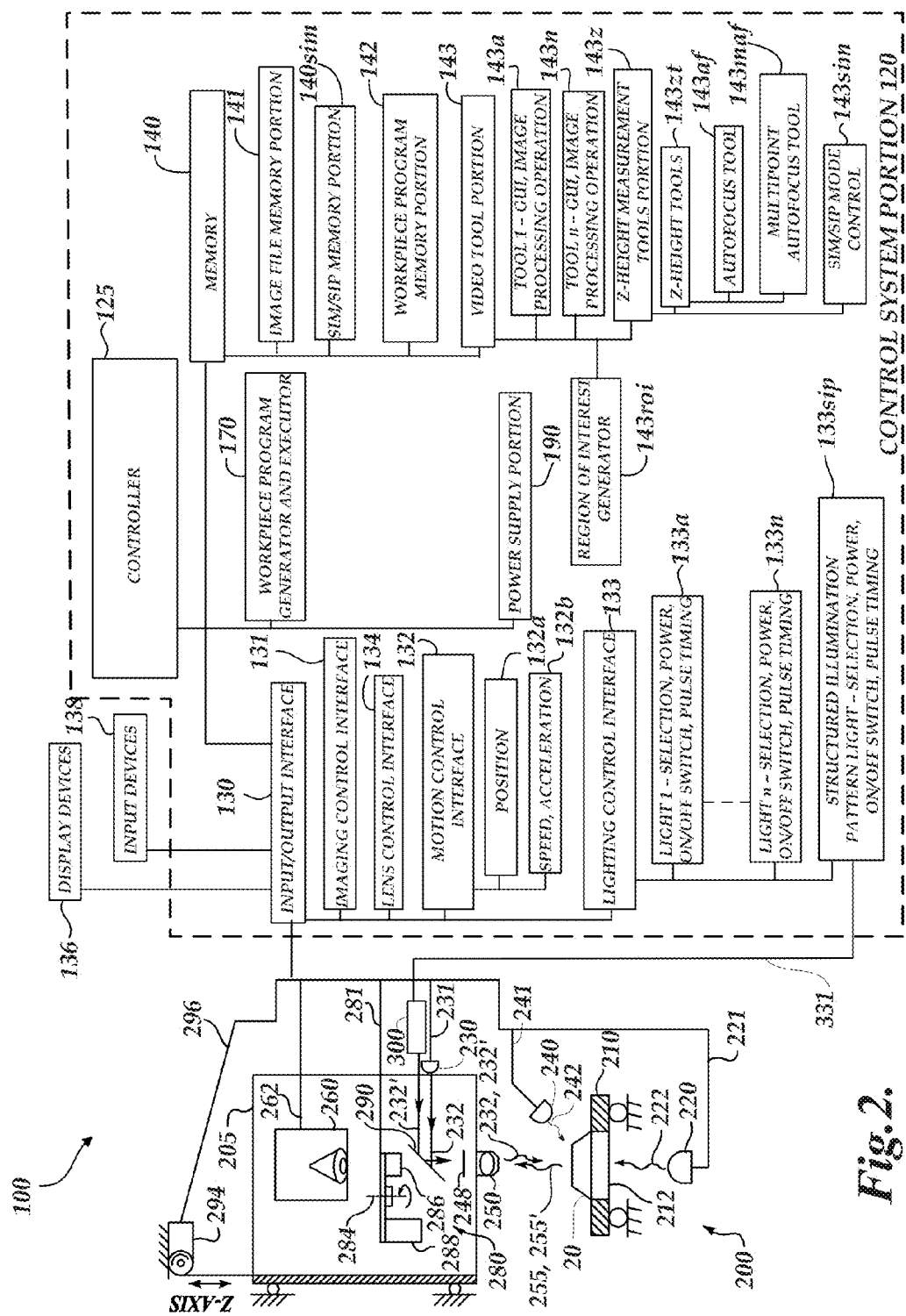
FIG. 2 is a block diagram of a control system portion and a vision components portion of a machine vision inspection system similar to that of FIG. 1, and including a structured illumination pattern generator and other features described herein.

FIG. 2 is a block diagram of a control system portion 120 and a vision components portion 200 of a machine vision inspection system 100 similar to the machine vision inspection system of FIG. 1, and including a structured illumination pattern generator and other features described herein. As will be described in more detail below, the control system portion 120 is utilized to control the vision components portion 200 and a controllable structured illumination pattern generating portion 300. The control system portion 120 may be arranged to exchange data and control signals with both the vision components portion 200 and the structured illumination pattern generating portion 300.

The vision components portion 200 includes an optical assembly portion 205, light sources 220, 230, and 240, and a workpiece stage 210 having a central transparent portion 212. The workpiece stage 210 is controllably movable along X and Y axes that lie in a plane that is generally parallel to the surface of the stage where a workpiece 20 may be positioned. The optical assembly portion 205 includes a camera system 260, an interchangeable objective lens 250, and may include a turret lens assembly 280 having lenses 286 and 288. Alternatively to the turret lens assembly, a fixed or manually interchangeable magnification-altering lens, or a zoom lens configuration, or the like, may be included.

The optical assembly portion 205 is controllably movable along a Z axis that is generally orthogonal to the X and Y axes, by using a controllable motor 294 that drives an actuator to move the optical assembly portion 205 along the Z axis to change the focus of the image of the workpiece 20. Of course, in other embodiments, the stage could be moved along the Z axis relative to a static optical assembly in a known manner. The controllable motor 294 is connected to the input/output interface 130 via a signal line 296.

A workpiece 20, or a tray or fixture holding a plurality of workpieces 20, which is to be imaged using the machine vision inspection system 100, is placed on the workpiece stage 210. The workpiece stage 210 may be controlled to move relative to the optical assembly portion 205, such that the interchangeable objective lens 250 moves between locations on a workpiece 20 and/or among a plurality of workpieces 20.

As will be described in more detail below, for certain SIM operations, the workpiece may be illuminated by SIP source light 232' provided from the structured illumination pattern generating portion 300. The structured illumination pattern generating portion 300 configures the structured illumination pattern that is output to the workpiece 20. One or more of a stage light 220, a coaxial light 230, structured illumination pattern generating portion 300, and a surface light 240 (e.g., a ring light) may emit source light 222, 232, 232', and/or 242, respectively, to illuminate the workpiece or workpieces 20. The light source 230 may emit source light 232 and the structured illumination pattern generating portion 300 may emit SIP source light 232' along a shared path including a beamsplitter 290, as described in greater detail with reference to FIG. 3. The source light is reflected or transmitted as workpiece light 255 and the workpiece light used for imaging passes through the interchangeable objective lens 250 and the turret lens assembly 280 and is gathered by the camera system 260. The image of the workpiece(s) 20, captured by the camera system 260, is output on a signal line 262 to the control system portion 120. The light sources 220, 230, 240 and the structured illumination pattern generating portion 300 may be connected to the control system portion 120 through signal lines or busses 221, 231, 241, and 331, respectively. To alter the image magnification, the control system portion 120 may rotate the turret lens assembly 280 along an axis 284 to select a turret lens through a signal line or bus 281.

In various exemplary embodiments, the optical assembly portion 205 is movable in the vertical Z-axis direction relative to the workpiece stage 210 using a controllable motor 294 that drives an actuator, a connecting cable, or the like, to move the optical assembly portion 205 along the Z axis to change the focus of the image of the workpiece 20 captured by the camera system 260. The term Z axis, as used herein, refers to the axis that is intended to be used for focusing the image obtained by the optical assembly portion 205. The controllable motor 294, when used, is connected to the input/output interface 130 via a signal line 296.

As shown in FIG. 2, in various exemplary embodiments, the control system portion 120 includes a controller 125, an input/output interface 130, a memory 140, a workpiece program generator and executor 170, and a power supply portion 190. Each of these components, as well as the additional components described below, may be interconnected by one or more data/control buses and/or application programming interfaces, or by direct connections between the various elements.

The input/output interface 130 includes an imaging control interface 131, a motion control interface 132, a lighting control interface 133, and a lens control interface 134. The motion control interface 132 may include a position control element 132a and a speed/acceleration control element 132b, although such elements may be merged and/or indistinguishable. The lighting control interface 133 includes lighting control elements 133a-133n that control, for example, the selection, power, on/off switch, and strobe pulse timing, if applicable, for the various corresponding light sources of the machine vision inspection system 100. The lighting control interface 133 also includes a lighting control element 133sip that, in the illustrated embodiment, works in conjunction with the structured illumination pattern (SIP) generating portion 300 to provide structured illumination during image acquisitions, and particularly during a SIM mode image acquisitions, as described in greater detail below.

The memory 140 may include an image file memory portion 141, a SIM/SIP memory portion 140sim, a workpiece program memory portion 142 that may include one or more part programs, or the like, and a video tool portion 143. The video tool portion 143 includes video tool portion 143a and other video tool portions (e.g., 143n) that determine the GUI, image processing operation, etc., for each of the corresponding video tools, and a region of interest (ROI) generator 143roi that supports automatic, semi-automatic and/or manual operations that define various ROIs that are operable in various video tools included in the video tool portion 143.

In the context of this disclosure, and as known by one of ordinary skill in the art, the term video tool generally refers to a relatively complex set of automatic or programmed operations that a machine vision user can implement through a relatively simple user interface (e.g., a graphical user interface, editable parameter windows, menus, and the like), without creating the step-by-step sequence of operations included in the video tool or resorting to a generalized text-based programming language, or the like. For example, a video tool may include a complex pre-programmed set of image processing operations and computations which are applied and customized in a particular instance by adjusting a few variables or parameters that govern the operations and computations. In addition to the underlying operations and computations, the video tool comprises the user interface that allows the user to adjust those parameters for a particular instance of the video tool. For example, many machine vision video tools allow a user to configure a graphical region of interest (ROI) indicator through simple "handle dragging" operations using a mouse, in order to define the location parameters of a subset of an image that is to be analyzed by the image procession operations of a particular instance of a video tool. It should be noted that the visible user interface features are sometimes referred to as the video tool, with the underlying operations being included implicitly.

The video tool portion 143 also includes Z-height measurement tools portion 143z, which provides various operations and features related to Z-height measurement operations, as described in greater detail below. In one embodiment, the Z-height measurement tools portion 143z may include Z-height tools 143zt and Z-height tools SIM/SIP mode control 143sim. The Z-height tools 143zt may include an autofocus tool 143af, and a multipoint autofocus tool 143maf, for example. The Z-height tools SIM/SIP mode control 143sim may govern certain aspects of image stack acquisition and related structured light pattern generation operations in conjunction with the Z-height tools that are configured in a mode that determines best focus heights and/or Z-height measurements based on SIM techniques (e.g., as described further below).

Briefly, the Z-height measurement tools portion 143z may perform at least some operations similarly to known Z-height measurement tools, for example, performing operations in learn mode and run mode for generating all or part of a focus curve, and finding its peak as a best focus position. The Z-height measurement tools portion 143z may perform at least some operations similarly to known Z-height measurement tools, for example, performing operations in learn mode and run mode for generating all or part of a focus curve, and finding its peak as a best focus position. Additional Z-height measurement tool operations which are the subject of this disclosure are described in greater detail below.

Alternative configurations are also possible for the Z-height measurement tools portion 143z. For example, the Z-height tools 143zt may provide additional Z-height measurement tool elements, or the Z-height tools may have a selectable mode option that controls whether they are configured to operate in a conventional contrast-based analysis mode that uses conventionally lighted images (e.g., using the light source 230 to provide source light 232), or a SIM-based analysis mode that uses images lighted with specific structured illumination patterns (e.g., using the structured illumination pattern generating portion 300 to provide SIP source light 232'). In either case, the SIM/SIP mode control 143sim may provide operations that govern the user interface and interrelationships of the Z-height measurement tool elements in a manner that corresponds to their operating mode and/or use of SIM image acquisition and analysis techniques. More generally, this invention may be implemented in any now known or later-developed form that is operable in conjunction with the machine vision inspection system 100 to provide the features disclosed herein in relation to measurement operations based on SIM image acquisition and analysis techniques.

Figure 3:
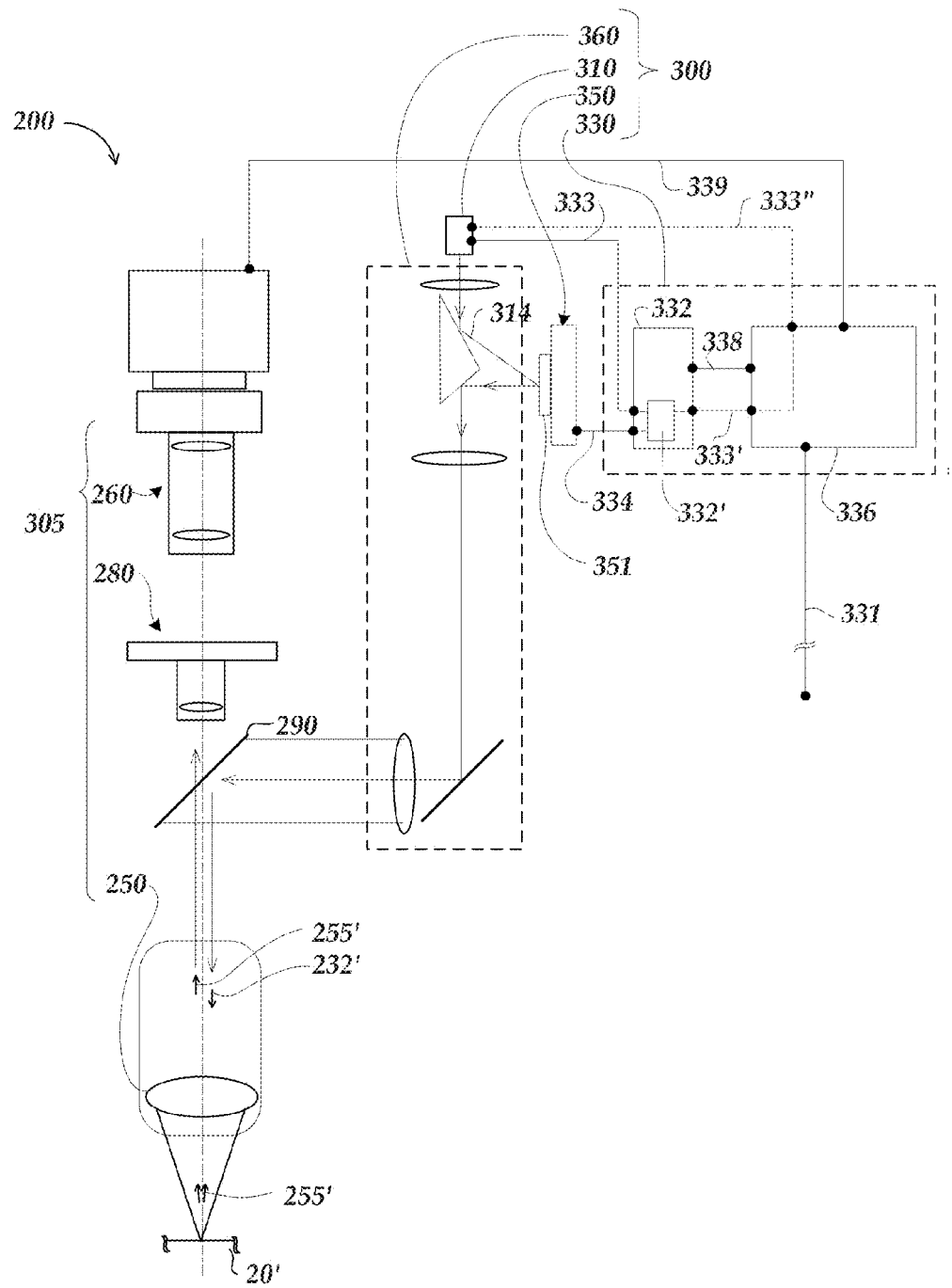
FIG. 3 is a block diagram including one exemplary embodiment of the structured illumination pattern generator shown in FIG. 2.

The signal line 262 from the camera system 260 and the signal line 296 from the controllable motor 294 are connected to the input/output interface 130. In addition to carrying image data, the signal line 262 may carry a signal from the controller 125 or elsewhere that initiates image acquisition. One or more display devices 136 (e.g., the display 16 of FIG. 1) and one or more input devices 138 (e.g., the joystick 22, keyboard 24, and mouse 26 of FIG. 1) can also be connected to the input/output interface 130. The display devices 136 and input devices 138 can be used to display a user interface, which may include various graphical user interface (GUI) features that are usable to perform inspection operations, and/or to create and/or modify part programs, to view the images captured by the camera system 260, and/or to directly control the vision system components portion 200. The display devices 136 may display user interface features associated with the video tools FIG. 3 is a block diagram showing a portion of the vision system components portion 200 of FIG. 2, including showing additional details of one exemplary embodiment of the structured illumination pattern generator 300, which may be used to implement various pattern generation and image exposure methods disclosed and claimed herein. In the illustrated embodiment, the structured illumination pattern generating portion 300 comprises a SIP optical portion 360, a light generator 310, a spatial light modulator (SLM) 350 that includes a controllable pixel array 351 that is configured in various patterns to create a pattern of transmitted and/or blocked light, and a SIP controller 330. The SIP controller 300 may include a timing and synchronization portion (TSP) 336 and an SLM controller portion 332 that may include a grayscale pattern sequencer 332'. The SLM controller portion 332 may be connected to the SLM 350 and the light generator 310, and the TSP 336, for example, through signal lines or busses 334, 333, and 338, respectively.

In operation, the light generator 310 may emit light 314 through a first part of the SIP optical portion 360 such that it is properly configured (e.g., collimated) to illuminate an illumination area the pixel array 351 of the SLM 350. The SLM 350 may then generally transmit, partially transmit, or block light according to known methods, to transmit or project a desired pattern along an optical path through the remainder of the SIP optical portion 360. As shown in FIG. 3, the projected pattern is output from the SIP optical portion 360 to be input to the beamsplitter 290 where it is directed as coaxial light through the objective lens 250 to provide SIP source light 232' to illuminate the field of view.

In some embodiments, the SLM 350 may comprise a transmissive LCD-type array, such as a micro-display graphics array from Forth Dimension Displays headquartered in Dalgety Bay, Fife, Scotland, United Kingdom, which includes an LCD pixel array that may generally be controlled by conventional video signals, if desired, and may be used to display an electronically generated 8-bit grayscale pattern that may transmit, partially-transmit, or block the light 314 through any given pixel of the pattern, depending on its grayscale value. However, the methods disclosed herein may be used to enhance certain advantages associated with an SLM 350, comprising an arrangement of any now-known or later-developed type of controllable reflective shutters that can provide controllable light deflection in a desired pattern. One type of controllable reflective shutter array that may be used includes liquid crystal on silicon (LCOS) micro-display products, for example, from Forth Dimension Displays headquartered in Dalgety Bay, Fife, Scotland. Various embodiments described below generally incorporate another type of array, which is digital micromirror device (DMD). DMDs and associated components are available, for example, from Texas Instruments DLP Products, Plano, Tex. DLP generally stands for digital light processing, which is associated with the fact that the array elements in DMD devices are either in an "on" position or "off" position, and projected/transmitted grayscale patterns must be generated over a time as an accumulated sequence of superimposed binary patterns. The systems and methods disclosed herein are particularly advantageous for overcoming certain deficiencies of known DLP control methods, and more particularly in relation to enhancing the accuracy of SIM techniques that are used to provide high accuracy measurements and the like.

In various embodiments, the light generator 310 may be used in a strobe illumination mode of operation to provide a combination of a very fast light generator response time (in the μs or ns range) at suitable optical power levels. One example of a light generator 310 may include one or more high-intensity light emitting diodes (LEDs), such as one of the LEDs in the Luxeon™ product line, available from Philips Lumileds Lighting Company of San Jose, Calif.

In the embodiment shown in FIG. 3, the SLM 350 may be a commercially available DMD, and the SLM controller portion 332 may be a companion digital controller chip, such as the chip sets available from Texas Instruments DLP Products referenced above. The SLM controller portion 332 may respond to desired grayscale pattern definitions or requests, and generate the synchronized control signals to the SLM 350 and the light generator 310 that provide the accumulated sequence of superimposed binary patterns that generate the desired grayscale pattern over time. However, commercial SLM controllers have certain deficiencies, for example, as summarized previously in the "Background" section of this disclosure and as further outlined with reference to FIG. 4 below. In the illustrated embodiment, the TSP 336 is used in conjunction with the SLM controller portion 332 to overcome or reduce these deficiencies, for example, by allowing the grayscale control finer than 256 bits, and/or other advantages, in some embodiments or implementations. In various embodiments, the TSP 336 may receive grayscale pattern and exposure level requests or control signals from the SIP lighting control element 133$sip$, and/or the SIM/SIP memory portion 140$sim$ (which may store predetermined or learned control signal configurations or parameters related to various desired patterns), over the line or buss 331. The TSP 336 may then process the received signals and send multiple incremental grayscale pattern requests to the SLM controller portion 332, such that the SLM controller portion 332 may generate each of the incremental grayscale patterns with 256 bit resolution over time, using its native control routines and circuits to control the SLM 350 and the light generator 310. The TSP 336 may thus control an overall image exposure achieved by the multiple incremental grayscale patterns because it may control the number of incremental requests within an image integration period of the camera 260, which it may exchange control signals with over the line 339. In various embodiments, some of the incremental requests may be for identical patterns and/or exposure increments. In some embodiments, one or more of the incremental requests may be for different patterns and/or exposure increments. Greater than 256-bit grayscale resolution for the illumination pattern may be achieved in this manner, if desired. In general, it is desirable that the TSP 336 provides dedicated processing and deterministic timing in relation to the control signals it receives and/or sends to various components. In some embodiments, the TSP 336 may therefore comprise a programmable logic array or the like. In some (optional) embodiments, rather than the SLM controller portion 332 directly controlling the light generator 310, the line 333 may be omitted and a light control timing signal from the SLM controller portion 332 may be output to the TSP 336 on the line 333', and the TSP 336 may control the light generator 310 over the line 333", based on the timing signal from the SLM controller portion 332. This may allow providing additional features and/or precise customized control of the light generator 310 within the timing window required by the native operations of the SLM controller portion 332. Various features and operations outlined above, are described in greater detail below.

Figure 4:
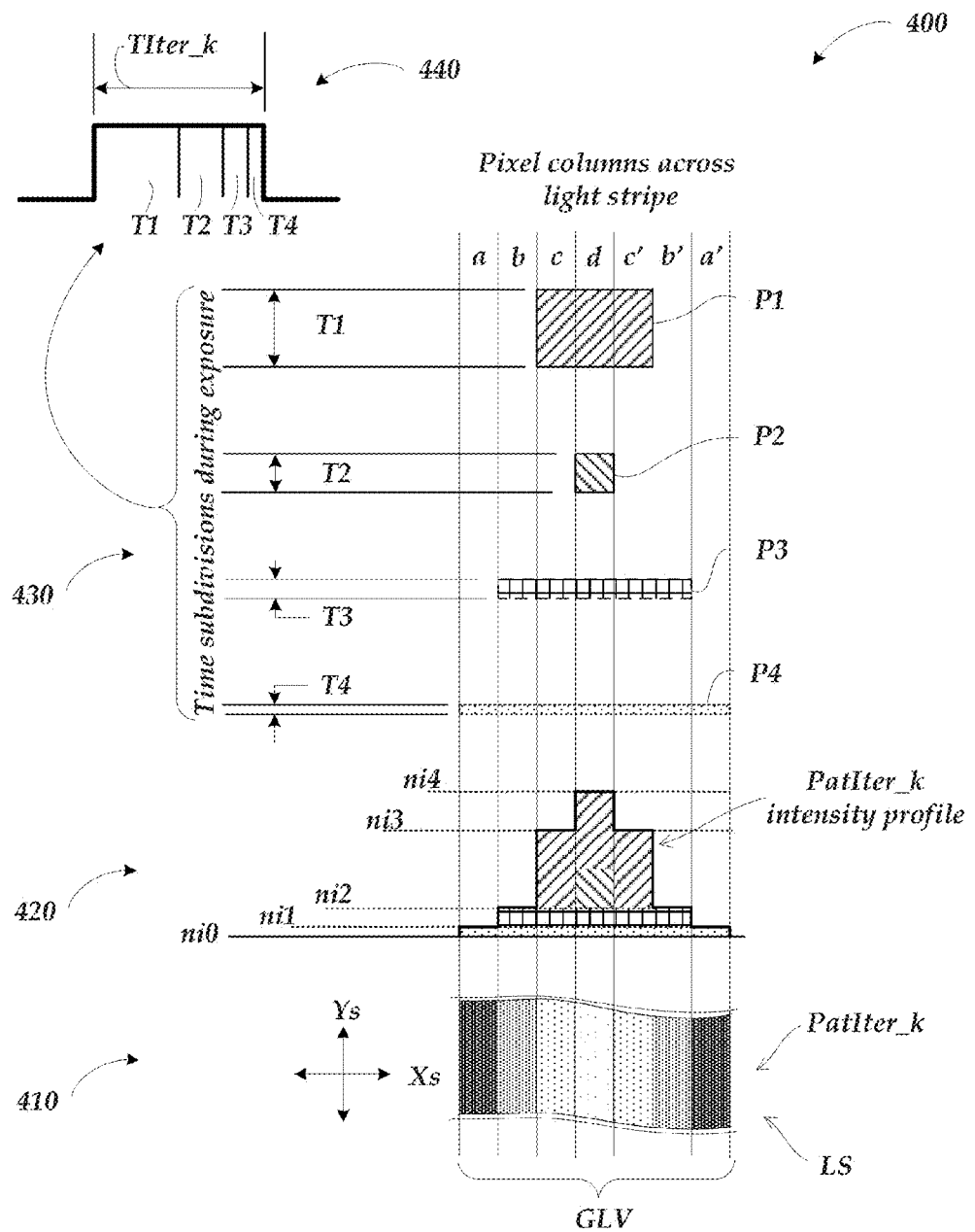
FIG. 4 is a diagram schematically representing one typical method used in a spatial light modulator such as that shown in FIG. 3, for a gray level illumination pattern generation sequence during an image exposure period.

FIG. 4 is a diagram 400 schematically representing one typical native control method used with a spatial light modulator such as the spatial light modulator 350 shown in FIG. 3, for projecting a gray level pattern of illumination during an image exposure period. In particular, FIG. 4 schematically represents the generation of a roughly sinusoidal gray level intensity variation GLV across a single structured illumination light stripe LS1, as created by a DLP device such as a digital micromirror device.

The diagram 400 illustrates a pattern subdivision exposure sequence 430 comprising a plurality of respective pattern portions P1-P4 (also referred to as subdivision pattern portions) exposed using respective iteration intensities of radiation from a light generator during respective iteration subdivision times T1-T4, respectively. The pattern subdivision exposure sequence 430 builds a simple 4-bit gray level sine wave pattern for the purpose of illustrating the basic principles that are relevant to this disclosure.

The diagram 400 includes corresponding elements that are vertically aligned along "pixel columns across light stripe." A truncated "plan view" shows a roughly sinusoidal gray level intensity variation GLV across the single structured illumination light stripe LS 1, which is a stripe extending along the direction Ys. The lighter and darker shadings across the stripe LS represent the accumulated exposure or net intensity resulting from the intensity pattern subdivision exposure sequence 430, which is designated PatIter_k, indicating that it may correspond to a complete grayscale pattern exposure iteration or increment k (e.g., k=1, 2, 3 etc.) as described further below. This particular stripe is lightest along the pixel column d and darkest along pixel columns a and a'. Immediately above the plan view representation of PatIter_k, is a graph schematically representing the contributions to the net intensity profile across the PatIter_k. The graph uses crosshatch patterns that are coded to be the same as the crosshatch patterns used to indicate the pixel columns that are activated to provide the respective subdivision pattern portions P1-P4 during respective subdivision times T1-T4. It is assumed that the light generator is set to the same intensity for each of the times T1-T4, such that the accumulated intensity is proportional to the times. The times T1-T4 are binary subdivisions, that is T3=2*T4, T2=2*T3, and T1=2*T2. It is shown that the pixels of the brightest Col. d are "on" in each of the subdivision pattern portions P1-P4, to provide the net intensity ni4. The pixels of the next brightest columns c and c' are "on" in each of the subdivision pattern portions, except P2, to provide the net intensity ni3. The pixels of the next brightest columns b and b' are "on" only in the subdivision pattern portions P3 and P4 to provide the net intensity ni2, and the darkest columns a and a' are on only in the subdivision pattern portion P to provide the net intensity ni1. The timing diagram 440 shows that the total time to generate the gray level strip pattern PatIter_k is TIter_k, assuming negligible time between the time periods T1-T4, for the purposes of this illustration. It will be appreciated that latency times, delays, and the like may be calibrated or determined for particular machines, light generators, voltage levels, etc., by design and/or experiment, and the results calibrated or stored (e.g., in the SIM/SIP memory portion 140$sim$, such that a combination of timing, operating voltages, and the like, that provide a desired or calibrated illumination level may be readily determined and/or compensated for (e.g., in the operation of the SIP controller 330).

The typical native control method outlined above may be used in DLP controllers (e.g., in a digital DMD controller) that adjust the overall time TIter_k, and/or the light generator intensities used during the subdivision times to achieve a desired net gray level intensity pattern.

A general transfer function for a sine pattern exposure during a single image, as outlined above with reference to FIG. 4, may be expressed as:

$$\text{PatIter\_k} = [P1*I1*T1] + \ldots + [Pn*In*Tn] = \sum_{i=1}^{n} [Pi*Ii*Ti] \quad \text{(Eq. 1)}$$

Where PatIter_k=the "k"th iteration of a complete gray level pattern (e.g., a stripe having a sinusoidal gray level intensity profile across the stripe), within an image exposure period; Ti=a pattern generation time subdivision (e.g., one of the time subdivisions T1-T4 as illustrated in FIG. 4); Pi=Pattern subdivision i (e.g., the partial pattern of SLM pixels that is on during one of the pattern generation time subdivisions Ti (e.g., one of the pattern subdivisions P1-P4 as illustrated in FIG. 4); Ii=Light intensity during the time subdivision Ti. In certain configurations, binary time subdivisions are implemented, such that Ti=T(i−1)/(2^(i−1)), and a constant intensity may be utilized throughout a single set of the pattern subdivisions, such that $I_1=I_2=I_n$, as implied in the illustration shown in FIG. 4.

The typical native control method outlined above which adjusts the overall time TIter_k, which is equivalent to increasing each of the times Ti and/or the light generator intensities Li used during the subdivision times, to achieve a desired net gray level intensity pattern increase. However, this approach leads to previously outlined deficiencies, and the inventor has found that SIM measurement accuracy may be sensitive to some selections of these variables that would be of no consequence in many other applications. Therefore, the typical native control method for DLP's is inadequate for certain high-resolution precision machine vision inspection operations, and certain high-accuracy SIM applications, in particular. Related problems and solutions are described in greater detail, below.

As a background for appreciating benefits of the systems and methods disclosed herein, FIGS. 5 and 6A-6D are used to briefly explain one exemplary known SIM technique for the purpose of illustrating the sensitivity of the technique to variations in the intensity and/or intensity profile of the structured illumination used for the analyzed images. FIG. 7 is used to explain a more subtle and underappreciated sensitivity to the structured illumination method that is relevant to certain applications of the SIM technique.

Figure 5:
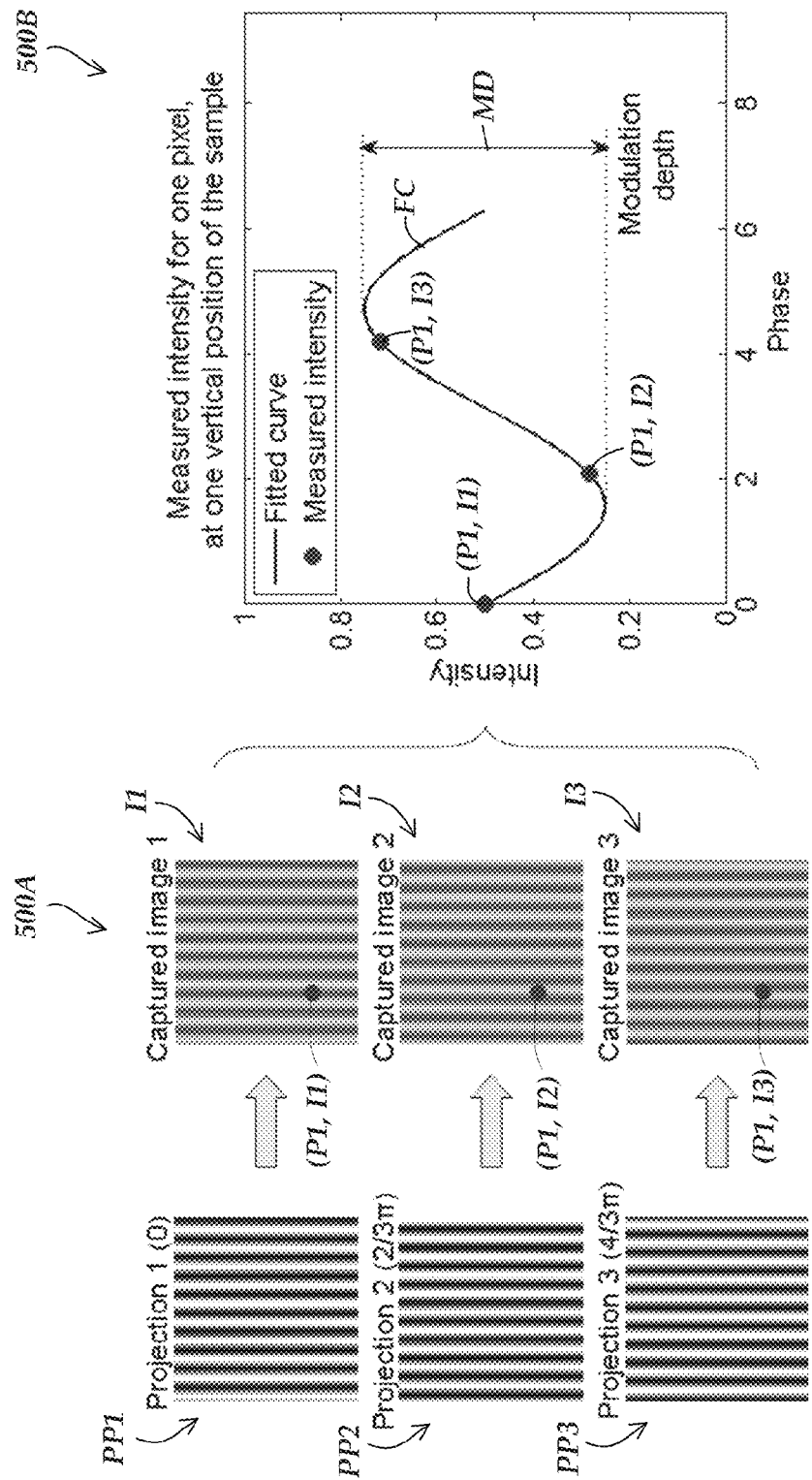
FIG. 5 is a diagram illustrating a known SIM technique comprising a sequence of three projected structured illumination patterns with different phases and corresponding captured images and an associated measured intensity curve of a single pixel for determining a modulation depth.

FIG. 5 is a diagram illustrating a known SIM technique. In the illustrated example, as shown in the illustration portion 500A the technique comprises projecting a sequence of three structured illumination patterns PP1-PP3 with different phases (e.g., an effective spatial phase shift of 120 degrees of the spatial period of the projected stripe pattern between phases) onto a workpiece and capturing corresponding images I1-I3. Assuming the same exposure level for each image and a repeatable sinusoidal intensity variation across the stripes in the projected stripe pattern in each image, then one would expect the results analogous to those shown in the illustration portion 500B at the same pixel location in each of the images I1-I3. In particular, according to the assumptions above, one expects the pixel location P1 to have an intensity in the images I1-I3 that is proportional to the intensity of three locations across the sinusoidal stripe-intensity profile, where the three locations are separated by 120 degrees of spatial phase shift. This is illustrated in 500B by the three intensity values (P1,I1), (P2,I2), and (P3,I3). The SIM technique then includes fitting a sinusoidal curve FC to the three intensity values for the pixel location P1. The amplitude of the resulting fit curve FC, also known as the modulation depth MD, will be greatest when the workpiece at the pixel location P1 is at the best focus position. This is because the stripe contrast will be blurred at focus positions away from the best focus position, so the modulation depth MD will be lower in that case.

FIGS. 6A-6D are diagrams illustrating a SIM technique using a sequence of steps similar to that of FIG. 5, at three different focus heights Za, Zb, Zc. An associated modulation depth curve MC is formed to determine a peak modulation Z height that is indicative of the best focus height and/or Zheight associated with particular pixel location on a workpiece.

Figures 6A, 6B, 6C:
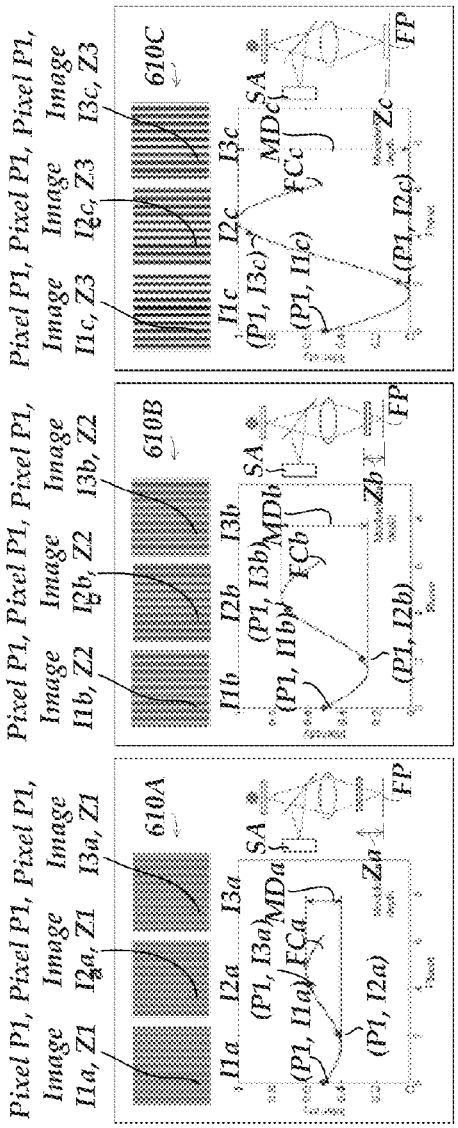
FIGS. 6A-6D are diagrams illustrating a SIM technique using sequences similar to that of FIG. 5 at three different corresponding focus heights and an associated modulation depth curve for determining a peak modulation indicative of the best focus height and/or Z height to be associated with the pixel.
Figure 7:
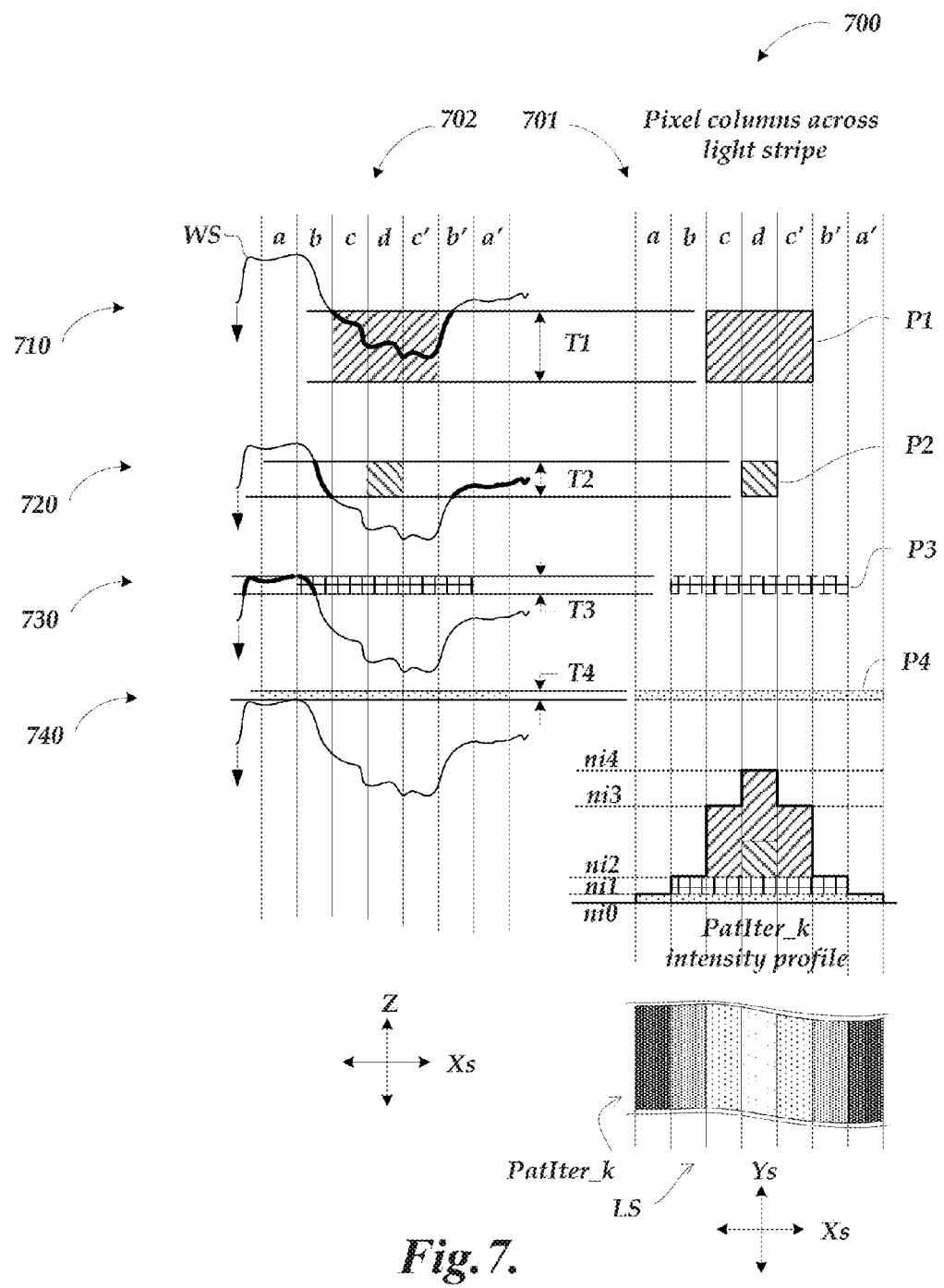
FIG. 7 is a diagram illustrating the typical gray level illumination pattern generation sequence shown in FIG. 4, in relation to illumination focus considerations that arise when illuminating a surface that is moving along the focus axis during an image exposure sequence.

As shown in FIG. 6A, a series 610A of three phase-shifted images I1a-I3a (that is, with the illumination pattern phase shifted) are captured at a vertical position Za. The small image of the optical system in FIG. 6A shows that the projected illumination arising from the source SA, as well as the imaging system, are focused at a plane FP and the Z height Za is far from FP. As a result the corresponding modulation depth MDa is relatively small. As shown in FIG. 6B, a series 610B of three phase-shifted images I1b-I3b are captured at a vertical position Zb. The small image of the optical system in FIG. 6B shows that the projected illumination arising from the source SA as well as the imaging system are focused at a plane FP, and the Z height Zb is closer to FP than was Za. As a result the corresponding modulation depth MDb is relatively larger than MDa. As shown in FIG. 6C, a series 610C of three phase-shifted images I1c-I3c are captured at a vertical position Zc. The small image of the optical system in FIG. 6C shows that the projected illumination arising from the source SA as well as the imaging system are focused at a plane FP, and the Z height Zc is approximated at FP. As a result the corresponding modulation depth MDc is approximately as large as possible.

Figure 6D:
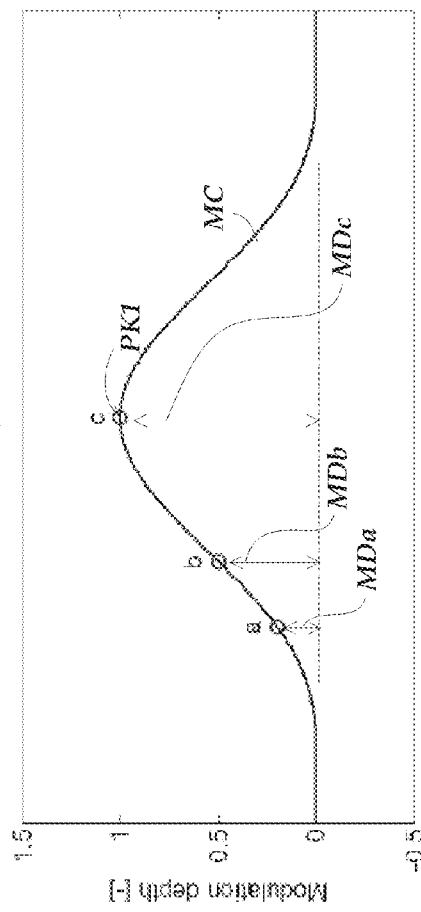

As shown in FIG. 6D, the modulation depths MDa-MDc are plotted against their corresponding Z heights (labeled vertical sample position), and a modulation depth curve MC is fitted to the plotted points. The peak of the modulation depth curve MC indicates the Z height where the corresponding pixel location on the workpiece is in focus.

The SIM techniques outlined above are known to be capable of producing high-resolution Z height measurements with high lateral resolution. However, as will be apparent to one skilled in the art, the accuracy of the techniques depends on fulfilling the assumptions that the intensity in each image is at the expected level (e.g., the same in each image, or otherwise known an compensated), and the intensity profile of the light stripe in each image is the same (and of a known shape). In one sense, the systems and methods disclosed are directed to better-fulfilling these assumptions over a wider exposure range in an economical manner. It should be understood that due to the high-resolution potential of the SIM technique, that even very small variations in the intensity and/or intensity profile are significant to the resulting accuracy.

FIG. 7 is a diagram 700 illustrating the typical gray level illumination pattern generation sequence shown in FIG. 4 in the illustration portion 701, in relation to illumination focus considerations shown in the illustration portion 702, which arise when illuminating a surface WS that is moving along the focus axis (the Z axis) during an image exposure sequence comprising the subdivision times T1-T4. In various applications, it is desirable to continuously scan the Z height of a workpiece relative to a best focus position, in order to capture SIM images such as those shown in FIGS. 5 and 6 with a high throughput. In contrast, stopping at a number of Z-height positions results in vibrations that disturb images and/or settling times that reduce throughput. It will be understood that for good results the scanning motion must be slow enough to support a relatively clear image exposure and support a comparable image exposure and Z height for each phase-shifted image that is used for determining a modulation depth corresponding to a particular Z height (or small range of Z heights). The following discussion illustrates a subtle problem that arises in relation to these considerations.

The illustration portion 701 and the terminology used below will be understood based on the previous description of FIG. 4. In illustration portion 702, the workpiece surface WS is represented as moving down at a constant speed in the figure relative to a focal plane of a structured illumination projection system and an imaging system. For purposes of the present discussion, it is assumed that for sufficient image exposure, the time TIter_k described with reference to FIG. 4 is extended (and, thus the subdivision times T1-T4 are extended) as required and a single iteration of the pattern is used for image exposure.

In the illustration portion 702, portions of the surface WS that pass through the best focus height for illumination and imaging are shown with a bold line. As shown in the first time-slice representation 710, during the subdivision T1, the portion of the surface WS that is illuminated and imaged at the best focus height as the surface WS moves down along the focus axis corresponds to the pixel columns c, d, and c' of the light stripe. It is seen that the portions of the surface corresponding to the pixel columns a, b, b', and a' of the light stripe are generally not well focused. They should receive very little of the subdivision pattern portion P1, but may receive a blurred "border" of the subdivision pattern P1, because they are "out of focus." In the second time-slice representation 720, during the subdivision T2, the portion of the surface WS that is illuminated and imaged at the best focus height as the surface WS moves down along the focus axis corresponds to the pixel columns b, b', and a' of the light stripe. It is seen that the portions of the surface corresponding to the pixel columns a, c, d, and c' of the light stripe are generally not well focused. They should receive very little of the subdivision pattern portion P2, but may receive a blurred "border" of the subdivision pattern P2 because they are "out of focus." In the third time-slice representation 730, during the subdivision T3, the portion of the surface WS that is illuminated and imaged at the best focus height as the surface WS moves down along the focus axis corresponds to the pixel column a of the light stripe. It is seen that the portions of the surface corresponding to the pixel columns b, c, d, c', b', and a' of the light stripe are generally not well focused. Except for column a', they should receive the subdivision pattern portion P3, but receive only a blurred version of the subdivision pattern P3 because they are "out of focus." In the fourth time-slice representation 740, during the subdivision T4, none of the surface WS is illuminated and imaged at the best focus height as the surface WS moves down along the focus axis. All columns should receive the subdivision pattern portion P4, but receive only a blurred version of the subdivision pattern P4 because they are all "out of focus" to varying degrees.

In the foregoing example and description, the Z-height relationships and effects are exaggerated to more clearly illustrate the problem. However, it will be understood that none of the workpiece surface (e.g., none of the pixel column locations a-a') receive the intended intensity contributions and/or provide the intended image contributions intended for the intensity profile PatIter_k due to the focus variations arising from the surface profile variation in combination with the Z motion during the subdivision times T1-T4. Stated another way, because of the way a gray level sine wave intensity profile is built over time by a typical DLP controller, different surface heights of the object may essentially receive a different "subdivision pattern" (i.e., an incomplete sampling of the sine pattern), which indicates that the height information (contrast, etc.) may be distorted. Or conversely, over the full exposure period, the image of the stripe may be "focus weighted" (e.g., blurred) differently in different regions in the subdivision patterns, and therefore does not exhibit the intended ideal sine profile. In certain implementations, this may be considered to violate the assumptions used in various previously outlined SIM equations and algorithms. These deleterious effects, which may disturb both the overall stripe intensity and the imaged stripe intensity profile apply to any image acquired during a Z motion, to some extent. The only solution that completely eliminates these problems is to stop the workpiece motion during each image acquisition (e.g., the times T1-T4), which is undesirable with regard to throughput considerations. An alternative, which significantly reduces the problem and increases accuracy, is described in greater detail below with reference to FIGS. 8 and 9.

The problem outlined with reference to FIG. 7 shows that the previously described typical (e.g., native) gray level illumination pattern generation sequence may limit accuracy and/or throughput when it stretches subdivision times to increase the exposure of an image (e.g., due to low surface reflectance or the like). It is desirable to avoid this. Furthermore, another potential downside to this kind of "native" control operation is that the overall projection duration may be different for each brightness level setting. These differences in duration of operation will vary heat generation of the structured illumination pattern generating portion and affect its repeatability between images. For example, the repeatability of the light generator spectrum (e.g., from one or more LEDs), and/or thermal expansion effects, and/or detector sensitivity and/or various circuit components may all be affected. Furthermore, another potential downside to this kind of "native" control operation is that the overall light generator intensity (whether controlled through drive current, or pulse width modulation, or both) may be different for each brightness level setting. In certain implementations dim scenes may require projection intensity or duty cycles levels close to 100% while highly reflective scenes may require intensity or duty cycles levels closer to 9%. However, any InGaN-based LED (blue, green, white), for example, will have a different emission spectrum based on the drive current and the pulse duration. Typical shifts in dominant wavelength are on the order of 2-3 nm without active heat sinks (e.g., Peltier coolers). Such variations may interact with detector sensitivities and/or workpiece reflectance sensitivity to wavelength to create unpredictable image intensity and/or spectrum variations from the expected values. It is desirable to avoid this.

Pattern brightness (global or local pattern attenuation) may also be varied by projecting with less than 8 bits. However, this strategy reduces the amplitude and resolution of the intensity profile of the projected sine patterns adversely affecting the signal to noise ratio of the technique, and may further violate the assumptions of SIM analysis if the shape of the intensity profile is actually altered by the reduced gray level resolution (e.g., due to digitization errors and the like.)

As will be described in more detail below with respect to FIGS. 8 and 9, an alternative method is provided for controlling the brightness of a structured illumination pattern (e.g., in an implementation utilizing SIM techniques). In various embodiments, a DLP controller is part of a system and method that controls the image brightness by causing the DLP controller to generate the required instances of gray level patterns using a relatively consistent on time (e.g., the time TIter_k). Instead of increasing an exposure level by increasing the on time of a single gray level pattern generation sequence, the method disclosed below causes the DLP controller to generate the gray level pattern sequence over a limited time, and then repeat the generation of the gray level pattern sequence for a number of iterations in order to achieve the desired exposure level. In one specific implementation of this method, a DMD (e.g., DLP5500) and control electronics (e.g., DLPC200, DLPA200), as well as an LED light generator, are operated at a relatively consistent maximum operating speed of the DMD. In one implementation, this is accomplished by dividing an image integration period into time periods in which complete structured illumination pattern iterations, including gray level variations, are generated and repeated. For example, some versions of the components referred to previously have the capability to generate 8-bit gray level patterns as fast as 716 Hz (~1.390 ms). A typical camera image acquisition frame rate may be 68 Hz (e.g., a camera integration period on the order of 14.705 ms). Consequently, these values may be up to approximately ten iterations of an 8-bit gray level pattern generation sequence (i.e., 14.705 ms/1.390 ms) in order to increase an exposure level during an image acquisition period. In one specific example implementation of this technique, the image integration period may be divided into 9 time periods (rather than 10, e.g., to allow for various time delays and latencies in the system), and at least some of the complete structured illumination pattern iterations that are repeated in the time periods may correspond to the components being operated at a high (in one implementation at the highest) operating speed of the DMD and its controller (e.g., ~11.1%×9~100% duty cycle). In this way, the heat generation and light emission spectrum are relatively constant, thus reducing variability in the projection components and the resulting structured illumination pattern.

Figure 8:
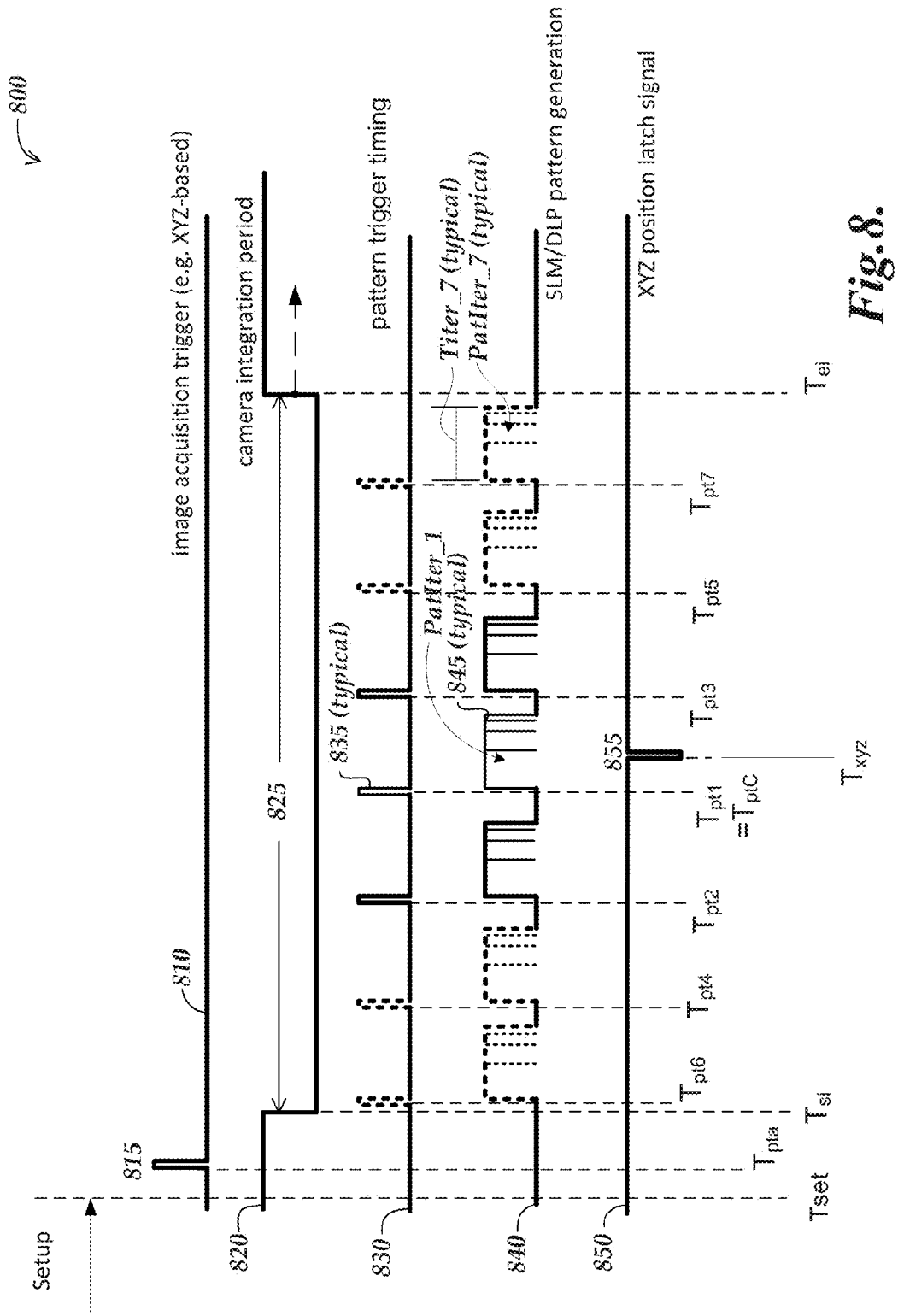
FIG. 8 is a timing diagram illustrating one exemplary embodiment of the methods disclosed herein for controlling a structured illumination pattern (SIP) generator such as that shown in FIG. 3, in order to generate a SIP that includes good grayscale resolution at a wide variety of exposure levels.

FIG. 8 is a timing diagram illustrating one exemplary embodiment of an image exposure comprising multiple structured illumination iterations according to methods disclosed herein for controlling a structured illumination pattern (SIP) generator such as that shown in FIG. 3 in order to generate a SIP that includes good grayscale resolution at a wide variety of exposure levels. FIG. 8 shows a timing chart 800 which includes five timelines. The timelines may start at a time Tset corresponding to the end of a setup, or reset, or initialization period following a previous iteration of the timelines (e.g., after a previous camera image transfer time, or the like). The first timeline 810 represents an image acquisition trigger signal 815 that may begin at a position trigger time Tpta based on positional X-, Y-, and Z-axis coordinates of the stage 210 (FIG. 2), which may correspond to a workpiece feature being positioned in the field of view of the camera 260, and/or a SIM-height determination scan along the Z axis being initiated, or the like.

The second timeline 820 represents a camera integration duration 825 that may have a controlled duration (Tei-Tsi). The controlled duration may be controlled based on a high-speed clock, such that it is relatively consistent. The camera integration duration 825 may start at integration begin time Tsi and end at integration end time Tei. In some implementations, the integration begin time Tsi may occur during a discrete latency period (Tsi-Tpta) after the position trigger time Tpta has been used to initiate a camera integration period. The latency period may be relatively consistent or predictable in various systems.

The third timeline 830 represents iterations of an illumination pattern trigger signal 835 that may occur at some or all of the times Tptk (where k=1 to 7 in this particular example), depending on the required exposure level, in order to trigger the corresponding gray level pattern generation sequence(s) represented by the signals 845 on the timeline 840. For example, in some embodiments, an illumination pattern trigger signal 835 may always be provided at the time TptC=Tpt1 at the "center" of the camera integration period, and corresponding to a time Txyz at which a position signal may be latched by a position latch signal 855 (shown on the timeline 850) to best represent the image position of the image acquired during the camera integration period (e.g., in case the camera and/or workpiece are moving during the image acquisition). The time Txyz may be set at a predetermined time delay relative to the pattern trigger signal time TptC, in various embodiments.

Each resulting gray level pattern generation sequence PatIter_k (e.g., PatIter-1 where k=1) may be thought of as a pattern generation sequence "iteration k," corresponding to PatIter_k in FIG. 4, that provides a corresponding increment of exposure. In the example outlined above, PatIter-1, due to its timing near the center of the integration time period, is the first-selected increment of exposure. For additional or increased exposure, additional illumination pattern trigger signals 835 may be provided. In one embodiment, the additional signals 835 may be selected to follow all or some of the selection sequence k=2, 3, 4, 5, 6, 7. It will be noted that this sequence does not follow a chronological order. Rather the selection of timings for the increments of exposure alternate to each side the center of the integration time period. In this case, the effective image exposure time as governed by the average of the selected illumination increment times will continue to tend toward the "central" time of the position latch signal 855, as pattern generation sequence iterations are added. In FIG. 8, for example, the solid line gray level pattern generation sequences 845 may provide the second and third exposure increments (corresponding to identifiers k=1, 2, 3), and the dashed line gray level pattern generation sequences 845 may provide the 4th-7th exposure increments, as needed (corresponding to increment identifiers k=4, 5, 6, 7). In some implementations, the pulse trigger time Tptk may be based on the same high-speed clock that is used to determine the camera integration duration 825.

It will be understood that the foregoing description is exemplary only and not limiting. As one example, more or fewer pattern generation iteration time periods may be provided during a camera integration period (e.g., 9 iterations, as outlined previously.) As another example, the selection sequence need not be as outlined above, and significant benefits will still be obtained. In one embodiment, circuits and/or routines corresponding to FIG. 3 may be used to provide the signals shown in FIG. 8. For example, the TSP may receive exposure level information for a particular exposure during the setup on the signal line 331. The signal 815 may be input to the TSP 336 on the line 331 and/or relayed by the TSP 336 to the camera 260 on the line 339. The TSP may further generate the trigger signals 835 corresponding to an exposure level information, and output them to the SLM controller portion 332 on the line 338. The SLM controller portion 332 may output corresponding signals to the SLM 350 on the line 334. The TSP 336 may generate the position latch signal 855 at the appropriate time and output it on the line 331. Other possible embodiments may be realized by one of ordinary skill in the art.

With reference to FIG. 7, it will be appreciated that if a gray level pattern generation sequence iteration k is executed in a short time (e.g., as shown FIG. 8), then if there is relative motion and focus change along the Z direction there will be less displacement during each subdivision time T1-T4 and each surface height will be exposed to a more complete or ideal "sampling" of the gray level pattern, such that the height information (contrast, etc.) will be less distorted. In other words, for each gray level pattern generation sequence iteration k, the image of a stripe is "focus weighted" more similarly in the different subdivisions, and therefore a surface image will exhibit characteristics that better correspond to the intended ideal sine profile (i.e., more closely approximating the assumptions used in the SIM equations and algorithms), resulting in improved accuracy.

The following description uses equations to outline and understand alternatives and/or preferences for providing structured illumination pattern iterations to provide exposure increments during an image acquisition, in various embodiments. Repeating Equation 1, outlined previously, a general transfer function for the "k"th full gray level pattern exposure increment during an image acquisition may be expressed as:

$$\text{PatIter\_k} = [P1 * I1 * T1] + \ldots + [Pn * In * Tn] = \sum_{i=1}^{n} [Pi * Ii * Ti] \quad \text{(Eq. 1)}$$

Thus, for an overall exposure of an image comprising a plurality of such exposure increments:

$$\text{TotalExposure} = \sum_{k=1}^{X} \text{PatIter\_k} \quad \text{(Eq. 2)}$$

Where X is a number of iterations or increments that provides the desired total exposure.

For convenience, we may define a reference or standard gray level pattern increment of exposure PatIter_std, which is generated in a standard time increment TIter_std, using a standard light intensity I_std as the light intensity Ii, for each of the time subdivisions Ti_std included in TIter_std. In one embodiment, we may select TIter_std to be approximately the minimum operable time for generating a full gray level pattern sequence using the native SLP controller. However, in other embodiments, TIter_std may be selected to be slightly longer, for reasons described below.

We may illustrate this reference or standard gray level pattern increment of exposure as:

$$\text{PatIter\_std} = \sum_{i=1}^{n} [Pi * I\_std * Ti\_std] \quad \text{(Eq. 3)}$$

As a first specific illustrative example, suppose it is desired to increase the exposure to a specific level, e.g., that is 3.2 times the exposure which is provided by one standard exposure increment PatIter_std. Two possible approaches that might be taken in typical native control methods are illustrated by:

$$3.2 * \text{PatIter\_std} = \sum_{i=1}^{n} [Pi * 3.2(I\_std) * Ti\_std] \quad \text{(Eq. 4)}$$

or $$3.2 * \text{PatIter\_std} = \sum_{i=1}^{n} [Pi * I\_std * 3.2(Ti\_std)] \quad \text{(Eq. 5)}$$

The methods illustrated by Equations 4 and 5 where only one exposure increment is used may be undesirable in that either the intensity or the overall projection timing period will be different for each brightness level setting. As previously outlined, these differences will vary the heat generation of the projection device and/or the LEDs and affect the overall system performance unfavorably. In addition, an InGaN-based LED (blue, green, white) will have a different emission spectrum based on the drive current and the pulse duration. Typical shifts in dominant wavelength are on the order of 2-3 nm without active heat sinks (e.g., Peltier coolers). Furthermore, with regard to the method illustrated by Equation 5, the length of time that each subdivision pattern is on is longer (e.g., 3.2 times in the above example), which indicates that if the focus height is changing at a high speed (e.g., as desired in some implementations), then the height sampling may become more non-uniform as outlined with reference to FIG. 7. In other words, each unique "non-sine" component or subdivision of the pattern is more likely to be the only pattern received by a surface region at a particular height while that height is in focus. Conversely, if it is desired for a particular surface region to receive the entire set of sub-patterns (so as to approach uniform gray level sine stripe sampling for all heights), then the Z speed would have to be reduced.

A better alternative, based on the principles disclosed herein, is illustrated by:

$$3.2 * \text{PatIter\_std} = \sum_{k=1}^{3} \text{PatIter\_std} + \sum_{i=1}^{n} [Pi * .2(I\_std) * Ti\_std] \quad \text{(Eq. 6)}$$

In one implementation, the method illustrated by Equation 6 may operate under the assumption that approximately the shortest possible times Ti are being used for Ti_std, such that one technique for achieving the "decimal part of the exposure" is to decrease the intensity during the last "0.2" pattern iteration (relative to the presumed standard intensity level I_std). The method illustrated by Equation 6 may also allow the height sampling to be more desirable as outlined with reference to FIG. 7 (i.e., a full gray level sine stripe pattern exposure is repeated 4 times throughout the exposure Z range, not just once), and the net intensity variation is made much smaller than that indicated for the method illustrated by Equation 5, in that the intensity is at a repeatable standardized level for three standardized exposure increments, or approximately 94% of the total exposure in this example. In various other implementations, it may be desirable for the intensity to never be reduced by amounts such as those indicated in the last term of Equation 6 (e.g., to avoid spectral variations.) Therefore, another alternative based on the principles disclosed herein, is illustrated by:

$$3.2 * \text{PatIter\_std} = \sum_{k=1}^{2} \text{PatIter\_std} + \sum_{i=1}^{n} [Pi * 1.2(I\_std) * Ti\_std] \quad \text{(Eq. 7)}$$

In one implementation, the method illustrated by Equation 7 indicates that the height sampling remains at a desirable level (e.g., a full gray level sine stripe pattern exposure is repeated three times throughout the exposure Z range, not just once), and there is only a relatively small intensity variation for just one increment of exposure.

Further alternative methods that may be implemented when the standard intensity I_std and/or the standard times Ti_std are defined to allow for some amount of additional increase and/or decrease in the system are illustrated by:

$$3.2 * \text{PatIter\_std} = \quad \text{(Eq. 8)}$$

$$\sum_{k=1}^{3} 1.067 * \text{PatIter\_std} = \sum_{k=1}^{3} \sum_{i=1}^{n} [Pi * \text{I\_std} * 1.067(\text{Ti\_std})]$$

$$3.2 * \text{PatIter\_std} = \quad \text{(Eq. 9)}$$

$$\sum_{k=1}^{3} 1.067 * \text{PatIter\_std} = \sum_{k=1}^{3} \sum_{i=1}^{n} [Pi * 1.067(\text{I\_std}) * (\text{Ti\_std})]$$

In various embodiments, a decision regarding whether to utilize one of the alternative methods illustrated by Equations 6, 7, 8, or 9 may be determined based on a matter of judgment regarding which provides the best tradeoff. For example, in various implementations, a "0.8" exposure portion may be best achieved with intensity reduction in one of the exposure increments (e.g., as in Equation 6), while a "0.2" exposure portion may be best achieved with a small intensity or time increase in one or more exposure increments (e.g., one of Equations 7, 8, or 9). Various other alternatives and combinations of intensity and time in various exposure increments will be apparent to one of ordinary skill in the art, based on the principles disclosed herein.

It will be appreciated that all of the methods illustrated by Equations 6, 7, 8, and 9 rely on a common principle of repeating an exposure pattern sequence not just once, but a plurality of times during an exposure. In various implementations, the repeated exposure pattern sequences may have an identical intensity and/or may have identical time periods. Certain of the repeated exposure pattern sequences may also be generated in the shortest possible time allowed by the pattern generating system.

It will be appreciated that the embodiments outlined above with reference to FIG. 8 and Equations 6-9 are exemplary only and not limiting. For example, as previously outlined, the number of time periods corresponding to a desired or maximum number of pattern generation sequence iterations within a camera integration period need not be seven, as in FIG. 8. Rather, it may be any desired number within the system operating capabilities (e.g., 9 periods as outlined previously, or 5, or 4, or may be adapted for a particular image exposure, or the like.) Of course, as previously implied, any member of a predetermined set of time periods may be set to provide a "zero exposure increment" (for example by omitting its trigger, or setting the source intensity to zero, or leaving the source intensity on and setting the pattern Pi to "off," or the like.) Furthermore, if an even number of exposure increments are to be selected from an odd number of time periods and used to achieve an overall exposure level, the "central" increment (e.g., corresponding to TptC and/or k=1 in FIG. 7) may be omitted in some embodiments. Similarly, if a single different "decimal portion" exposure increment is to be used to achieve a desired overall exposure level, the "central" increment (e.g., corresponding to TptC and/or k=1 in FIG. 7) may be selected to provide that different exposure increment in some embodiments. In such a case, a central position latch signal may then still be most appropriate for indicating the effective position of the image acquisition.

Figure 9:
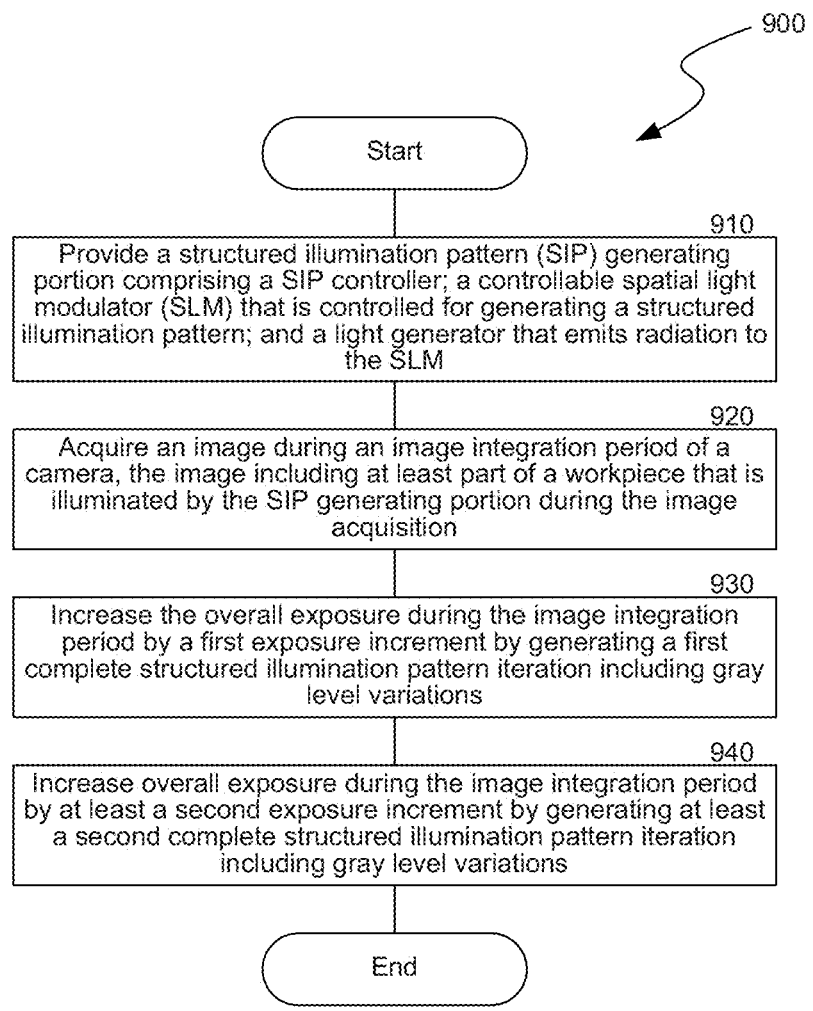
FIG. 9 is a flow diagram illustrating one exemplary embodiment of a routine for controlling a structured illumination pattern generating portion while acquiring an image.

FIG. 9 is a flow diagram illustrating one exemplary embodiment of a routine 900 for controlling a structured illumination pattern generating portion used to illuminate a workpiece with a structured illumination pattern during an image acquisition by a camera. At block 910, a structured illumination pattern (SIP) generating portion is provided comprising a SIP controller; a controllable spatial light modulator (SLM) that is controlled for generating a structured illumination pattern; and a light generator that emits radiation to the SLM. At block 920, an image is acquired during an image integration period of the camera, the image including at least part of a workpiece that is illuminated by the SIP generating portion during the image acquisition. At block 930, the overall exposure during the image integration period is increased by a first exposure increment by generating a first complete structured illumination pattern iteration including gray level variations. At block 940, the overall exposure during the image integration period is increased by at least a second exposure increment by generating at least a second complete structured illumination pattern iteration including gray level variations.

From the foregoing, it will be appreciated that specific embodiments of the invention have been described herein for purposes of illustration, but that various modifications may be made without deviating from the scope of the invention. For example, those skilled in the art will appreciate that the depicted flow chart may be altered in a variety of ways. More specifically, the order of the steps may be rearranged, steps may be subdivided and/or performed in parallel, steps may be omitted and alternative steps may be included, etc. Accordingly, the invention is not limited except as by the appended claims.

The invention claimed is:

1. A method for controlling a structured illumination pattern generating portion used to illuminate a workpiece with a structured illumination pattern during an image acquisition by a camera portion in a precision machine vision inspection system, wherein:

the structured illumination pattern (SIP) generating portion comprises:
    a SIP controller;
    a controllable spatial light modulator (SLM) that is controlled for generating the structured illumination pattern; and
    a light generator that emits radiation to the SLM; and
the method comprises:
    acquiring an image during an image integration period of the camera portion;
    increasing the overall exposure during the image integration period by a first exposure increment by generating a first complete structured illumination pattern iteration including gray level variations; and
    increasing the overall exposure during the image integration period by at least a second exposure increment by generating at least a second complete structured illumination pattern iteration including gray level variations.

2. The method of claim 1, wherein the second exposure increment and the first exposure increment are substantially the same.

3. The method of claim 2, wherein the method comprises operating the light generator to emit substantially the same radiation intensity during the first and second complete structured illumination pattern iterations.

4. The method of claim 3, wherein a ratio of the radiation intensity to a maximum controllable radiation intensity is greater than 0.6.

5. The method of claim 3, wherein the at least a second exposure increment further comprises a least-significant bit (LSB) exposure increment that is less than the first and second exposure increments.

6. The method of claim 5, wherein the method comprises operating the light generator to emit a first radiation intensity during the first and second complete structured illumination pattern iteration, and to emit an LSB radiation intensity that is less than the first radiation intensity during the complete structured illumination pattern iteration corresponding to the LSB exposure increment.

7. The method of claim 1, wherein the image integration period of the camera portion is a time period TIP, and the method comprises generating each complete structured illumination pattern iteration including gray level variations within a respective time period TCPi, wherein each respective time period TCPi is at most TIP/4.

8. The method of claim 7, wherein each respective time period TCPi is at most TIP/6.

9. The method of claim 7, wherein at least one of the respective time periods TCPi corresponds to the shortest possible time period allowed by the structured illumination pattern generating portion.

10. The method of claim 1, wherein the image integration period of the camera portion is a time period TIP comprising N equal subperiods TCPn, and the method comprises generating each complete structured illumination pattern iteration including gray level variations within a respective subperiod TCPn, and the method further comprises operating the structured illumination pattern (SIP) generating portion such that no exposure increment occurs within at least one respective subperiod TCPn.

11. The method of claim 1, wherein:
generating the first complete structured illumination pattern iteration comprises generating a first pattern subdivision exposure sequence comprising a plurality of respective pattern portions exposed using respective first iteration intensities of radiation from the light generator during respective first iteration subdivision times; and
generating the at least a second complete structured illumination pattern iteration including gray level variations comprises generating at least a second pattern subdivision exposure sequence comprising a plurality of respective pattern portions exposed using respective iteration intensities of radiation from the light generator during respective iteration subdivision times.

12. The method of claim 11, wherein at least the first and a second pattern subdivision exposure sequences are identical.

13. The method of claim 12, wherein:
the at least a second exposure increment further comprises an LSB exposure increment that is different than the first and second exposure increments; and
the method comprises generating the LSB exposure increment by generating a complete structured illumination pattern iteration including gray level variations by generating an LSB pattern subdivision exposure sequence comprising a plurality of respective pattern portions exposed using respective LSB iteration intensities of radiation from the light generator during respective LSB iteration subdivision times.

14. The method of claim 13, wherein the method includes at least one of (a) making the respective LSB iteration intensities less than the corresponding respective first and second iteration intensities, and (b) making the respective LSB iteration subdivision times less than the corresponding first and second iteration subdivision times.

15. The method of claim 13, wherein the method includes at least one of (a) making the respective LSB iteration intensities greater than the corresponding respective first and second iteration intensities, and (b) making the respective LSB iteration subdivision times greater than the corresponding first and second iteration subdivision times.

16. The method of claim 1, wherein the image integration period of the camera portion is a time period TIP comprising N subperiods TCPn, and the first and second complete structured illumination pattern iterations correspond to approximately a 100% duty cycle and are provided during one subperiod TCPn each, and
wherein an LSB structured illumination pattern corresponding to a duty cycle between 0% and 100% is provided during one subperiod TCPn, with structured illumination patterns corresponding to either a 0% or 100% duty cycle being provided during the remaining subperiods TCPn of the time period TIP.

17. The method of claim 1, wherein the SLM comprises a digital light processing array.

18. The method of claim 1, wherein the precision machine vision inspection system includes a structured illumination microscopy (SIM) mode of image acquisition and measurement, and the image is one of a stack of images that is acquired during the SIM mode of image acquisition and measurement.

19. A machine vision inspection system comprising:
a camera portion;
a structured illumination pattern (SIP) generating portion, comprising:
a SIP controller;
a controllable spatial light modulator (SLM) that is controlled for generating the structured illumination pattern; and
a light generator that emits radiation to the SLM;
a memory for storing programmed instructions; and
a processor configured to execute the programmed instructions to perform operations including:
acquiring an image during an image integration period of the camera portion;
increasing the overall exposure during the image integration period by a first exposure increment by generating a first complete structured illumination pattern iteration including gray level variations; and
increasing the overall exposure during the image integration period by at least a second exposure increment by generating at least a second complete structured illumination pattern iteration including gray level variations.

20. A non-transitory computer-readable storage medium with instructions stored thereon that are executable by a processor in a precision inspection system with a camera portion and a structured illumination pattern generating portion to perform operations of:
acquiring an image of a workpiece during an image integration period of the camera portion; and
controlling the structured illumination pattern generating portion to illuminate the workpiece with a structured illumination pattern during the image integration period of the camera portion, including:
increasing the overall exposure during the image integration period by a first exposure increment by generating a first complete structured illumination pattern iteration including gray level variations; and
increasing the overall exposure during the image integration period by at least a second exposure increment by generating at least a second complete structured illumination pattern iteration including gray level variations.

* * * * *